US012426870B2

(12) United States Patent
Girouard et al.

(10) Patent No.: US 12,426,870 B2
(45) Date of Patent: Sep. 30, 2025

(54) SURGICAL RETRACTOR

(71) Applicant: Advanced Surgical Retractor Systems, Inc., Shavano Park, TX (US)

(72) Inventors: Michael R. Girouard, Shavano Park, TX (US); Alice Stover Mayfield, Denver, CO (US); Shane Jerid Korthuis, Denver, CO (US); Marc Andrew Hanchak, Denver, CO (US)

(73) Assignee: Advanced Surgical Retractor Systems, Inc., Shavano Park, TX (US)

( * ) Notice: Subject to any disclaimer, the term of this patent is extended or adjusted under 35 U.S.C. 154(b) by 156 days.

(21) Appl. No.: 18/270,423

(22) PCT Filed: Jan. 3, 2022

(86) PCT No.: PCT/US2022/011044
§ 371 (c)(1),
(2) Date: Jun. 29, 2023

(87) PCT Pub. No.: WO2022/147505
PCT Pub. Date: Jul. 7, 2022

(65) Prior Publication Data
US 2024/0122590 A1    Apr. 18, 2024

Related U.S. Application Data

(60) Provisional application No. 63/133,408, filed on Jan. 3, 2021.

(51) Int. Cl.
*A61B 17/02*    (2006.01)

(52) U.S. Cl.
CPC ...... *A61B 17/0293* (2013.01); *A61B 17/0206* (2013.01)

(58) Field of Classification Search
CPC .................. A61B 17/0206; A61B 17/0293
See application file for complete search history.

(56) References Cited

U.S. PATENT DOCUMENTS

| 1,706,500 A | 3/1929 | Smith |
| 1,919,120 A | 7/1933 | Oconnor |

(Continued)

FOREIGN PATENT DOCUMENTS

| CN | 201939399 | 8/2011 |
| CN | 203001015 | 6/2013 |

(Continued)

OTHER PUBLICATIONS

PCT international preliminary report on patentability, PCT/US2022/011044, dated Jul. 4, 2023, The International Bureau of WIPO, Switzerland (21 pages).

(Continued)

*Primary Examiner* — Larry E Waggle, Jr.
(74) *Attorney, Agent, or Firm* — Pizarro Allen PC

(57) ABSTRACT

A surgical retractor assembly and related attachments are provided to assist in surgical procedures. The surgical retractor provides for increased flexibility and ease of assembly. The surgical retractor may, for example, comprise two frame segments configured so that they may be coupled together using a connector that allows one frame segment to be vertically positioned above a second frame segment and lowered onto the second frame segment so that a top surface of the second frame segment is received within a connector channel. The frame segments may thus be coupled together to form an adjustable frame.

15 Claims, 29 Drawing Sheets

(56) References Cited

U.S. PATENT DOCUMENTS

| | | | |
|---|---|---|---|
| 1,963,173 | A | 6/1934 | Paul |
| 2,013,892 | A | 9/1935 | Lucas |
| 2,053,868 | A | 9/1936 | Grosso |
| 2,751,902 | A | 6/1956 | Loeffler |
| 2,751,903 | A | 6/1956 | Ivory |
| 3,384,077 | A | 5/1968 | Gauthier |
| 3,724,449 | A | 4/1973 | Gauthier |
| 4,254,763 | A | 3/1981 | McCready |
| 4,424,724 | A | 1/1984 | Bookwalter |
| 4,852,552 | A | 8/1989 | Chaux |
| 5,231,974 | A | 8/1993 | Giglio |
| 5,520,610 | A | 5/1996 | Giglio |
| 5,865,731 | A | 2/1999 | Lenox |
| 6,322,500 | B1 | 11/2001 | Sikora |
| 6,468,207 | B1 | 10/2002 | Fowler, Jr. |
| 6,730,022 | B2 | 5/2004 | Martin |
| 6,808,493 | B1 | 10/2004 | Bookwalter |
| 6,958,038 | B2 | 10/2005 | Feng |
| 7,491,168 | B2 | 2/2009 | Raymond |
| 8,900,137 | B1 | 12/2014 | Lovell |
| 9,089,299 | B2 | 7/2015 | Nowak |
| 9,216,016 | B2 | 12/2015 | Fiechter |
| 9,498,198 | B2 | 11/2016 | Hu |
| 9,510,812 | B2 | 12/2016 | Brown |
| 2002/0183833 | A1 | 12/2002 | Stevens |
| 2003/0065251 | A1 | 4/2003 | Feng |
| 2004/0049101 | A1 | 3/2004 | Phillips |
| 2004/0092797 | A1 | 5/2004 | Yi |
| 2004/0230191 | A1 | 11/2004 | Frey |
| 2005/0096508 | A1 | 5/2005 | Valentini |
| 2006/0271096 | A1 | 11/2006 | Hamada |
| 2009/0287062 | A1 | 11/2009 | Farley |
| 2010/0280586 | A1 | 11/2010 | Case |
| 2012/0022335 | A1 | 1/2012 | Assaker |
| 2012/0296170 | A1 | 11/2012 | Wilkins |
| 2013/0082157 | A1 | 4/2013 | Agbodoe |
| 2013/0158359 | A1 | 6/2013 | Predick |
| 2013/0317312 | A1 | 11/2013 | Eastlack |
| 2014/0088370 | A1 | 3/2014 | Giulianotti |
| 2014/0114137 | A1 | 4/2014 | Reglos |
| 2016/0287234 | A1 | 10/2016 | Bass et al. |
| 2018/0234009 | A1 | 8/2018 | Cestero |
| 2019/0015089 | A1 | 1/2019 | Rosenbaum |
| 2020/0214686 | A1 | 7/2020 | Truckey |
| 2021/0346006 | A1 | 11/2021 | Cestero |

FOREIGN PATENT DOCUMENTS

| | | | |
|---|---|---|---|
| CN | 203815511 | | 9/2014 |
| DE | 202014003736 | | 5/2014 |
| EP | 1195141 | A2 | 4/2002 |
| EP | 1949860 | B1 | 7/2008 |
| EP | 2417922 | B1 | 2/2012 |
| EP | 2462883 | B1 | 6/2012 |
| EP | 2524662 | A2 | 11/2012 |
| EP | 2601898 | A2 | 6/2013 |
| JP | 2003-231550 | A | 8/2003 |
| JP | 2008531219 | | 4/2009 |
| JP | 2012040381 | | 3/2012 |
| WO | WO 90/01298 | | 2/1990 |
| WO | WO1990001298 | | 2/1990 |
| WO | WO 01/80725 | | 11/2001 |
| WO | WO2001080725 | | 11/2001 |
| WO | WO2010100592 | | 3/2009 |
| WO | WO2017027640 | | 2/2017 |
| WO | WO-2020061073 A1 * | | 3/2020 ......... A61B 17/0206 |

OTHER PUBLICATIONS

PCT International Search Report, PCT/US2022/011044, dated May 5, 2022, The International Bureau of WIPO, Switzerland (4 pages).

* cited by examiner

FIG. 8A  Connectors or ratchet subassemblies are assembled onto frame segment or upper arm segment and welded into place.

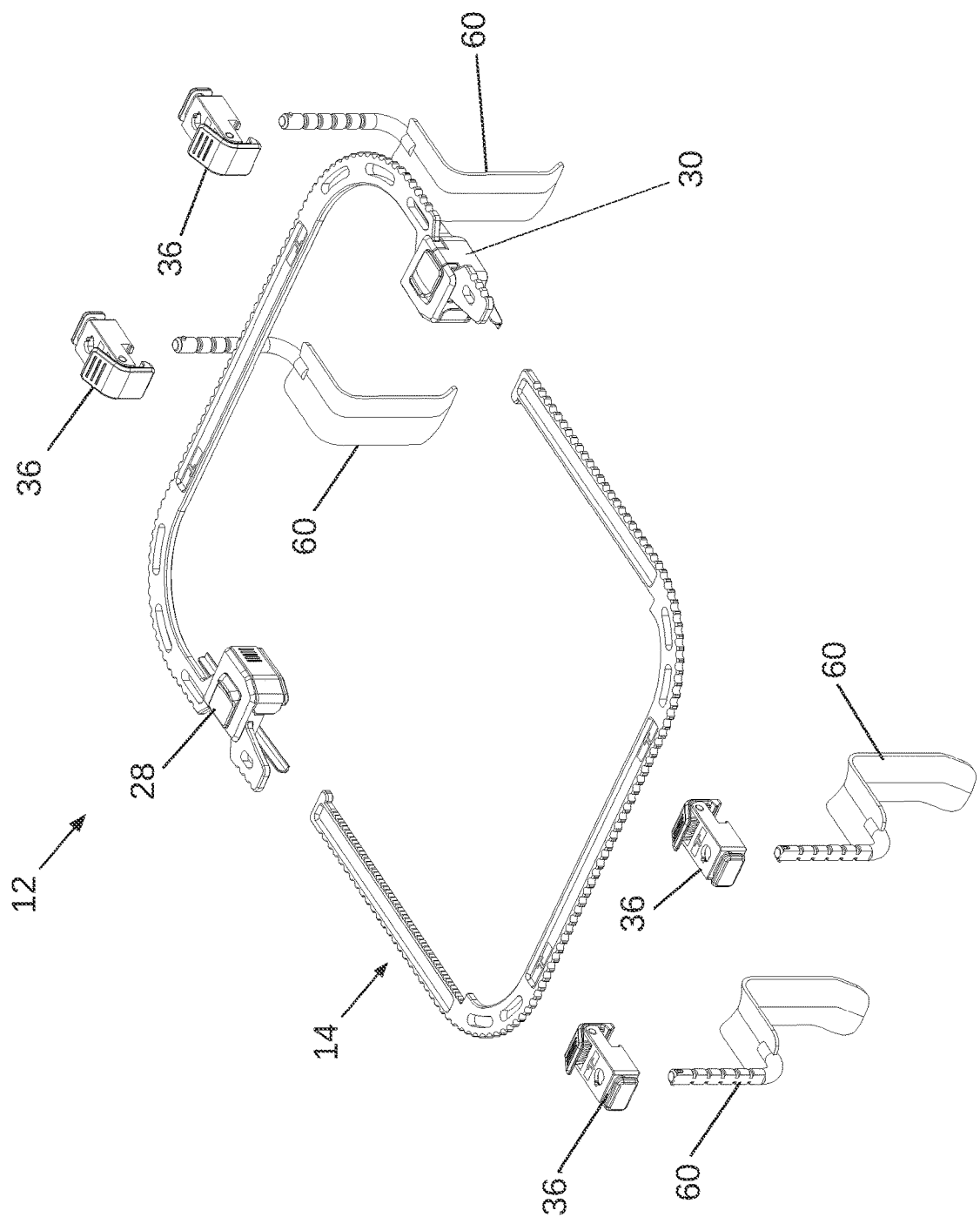

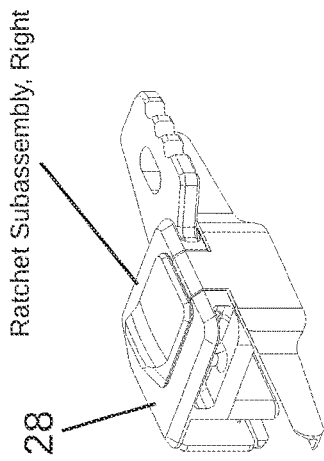
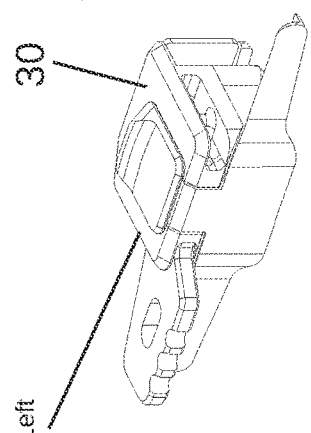
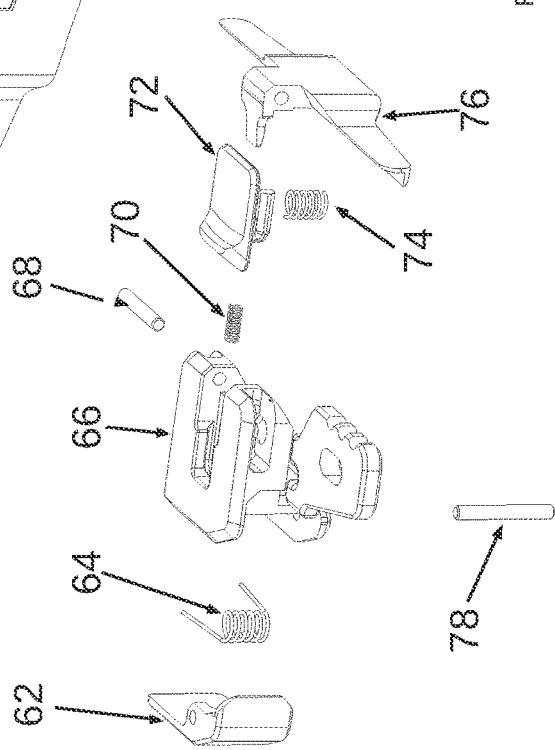

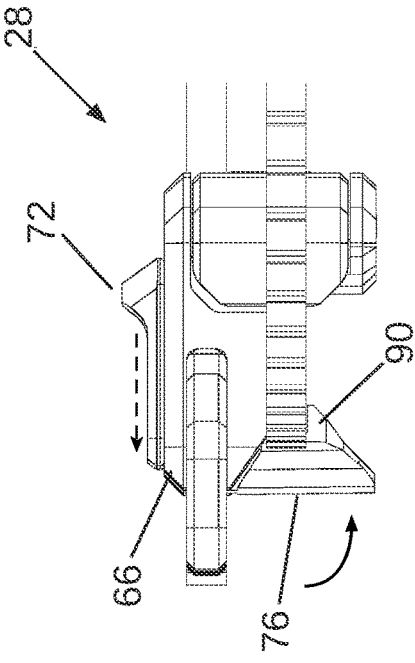
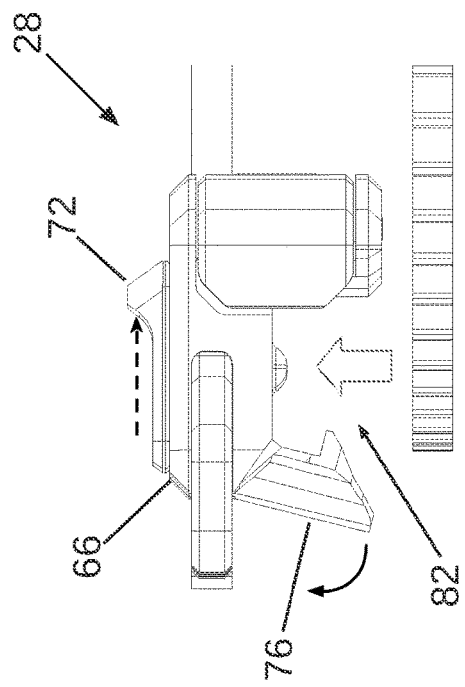
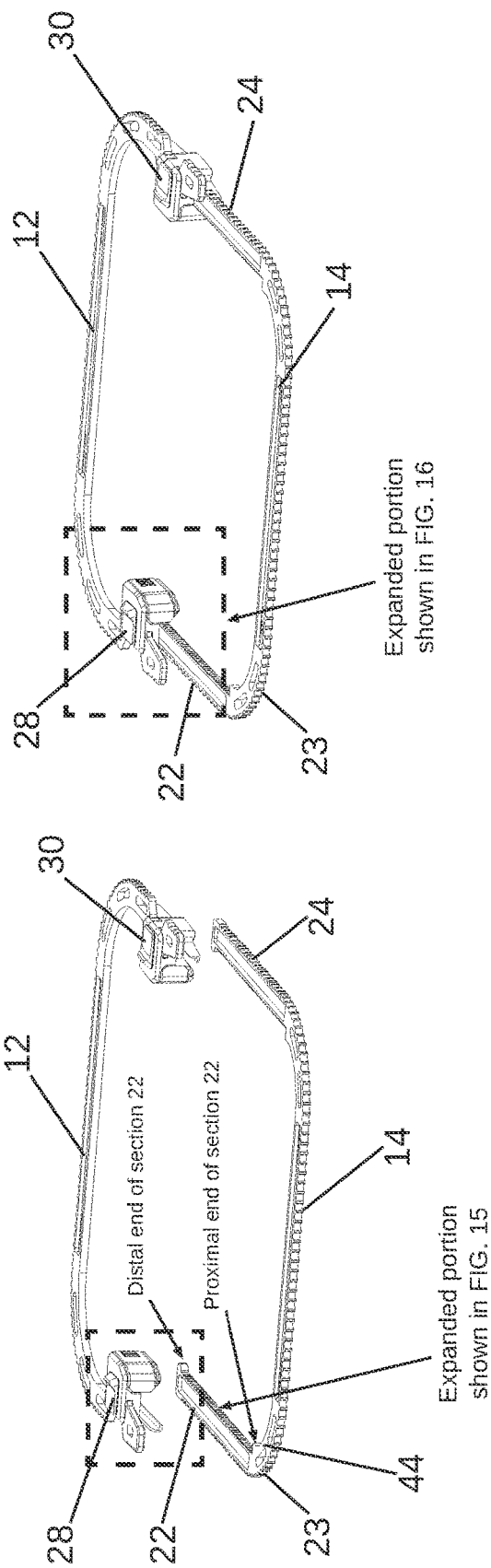
FIG. 14

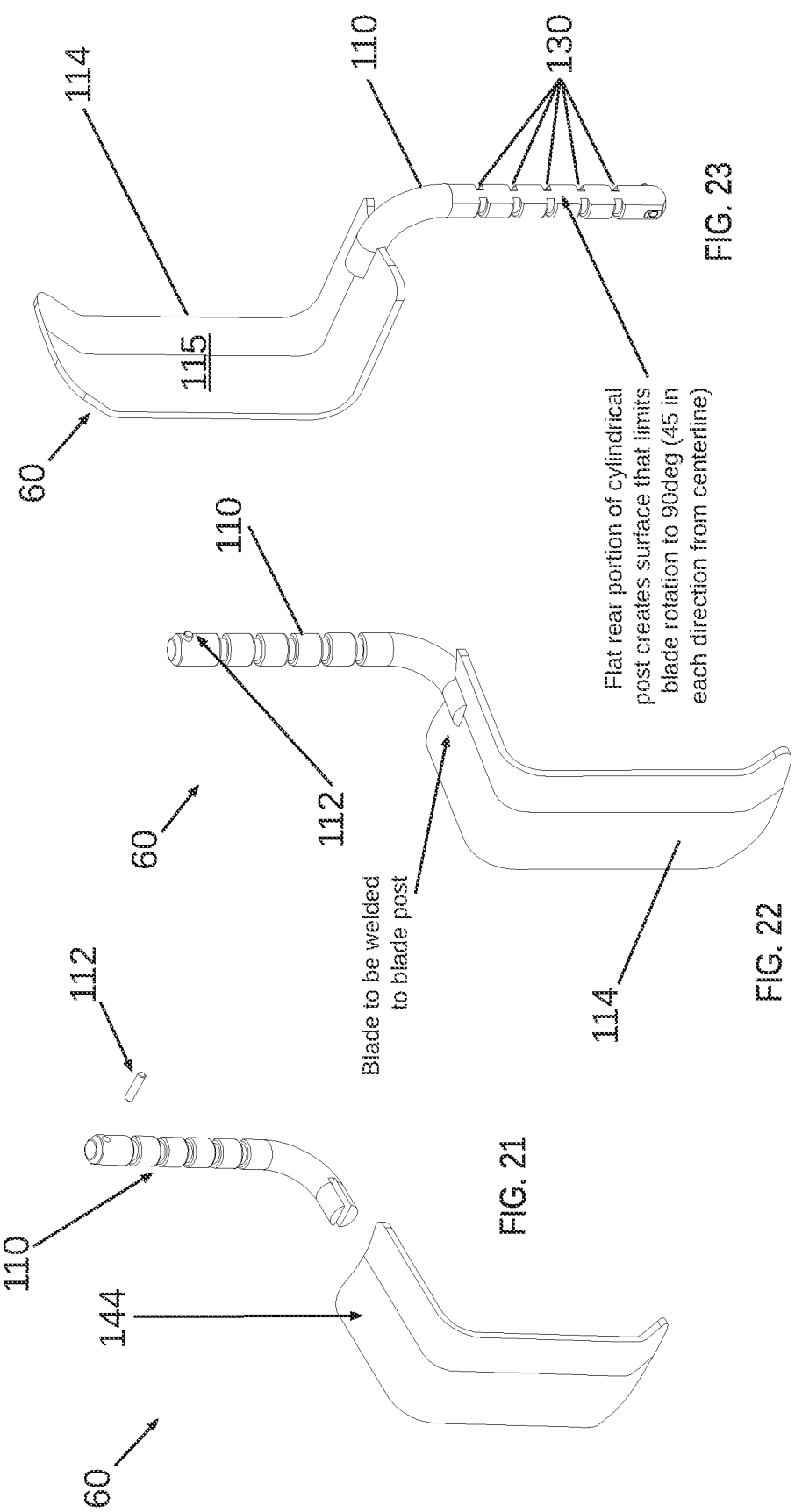

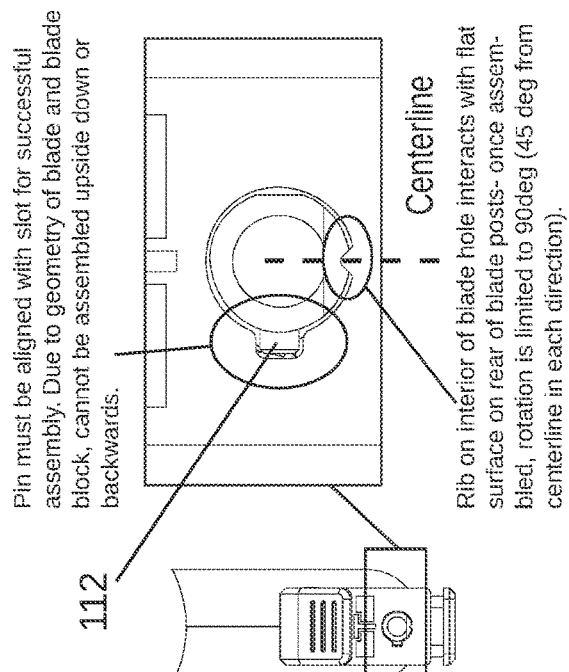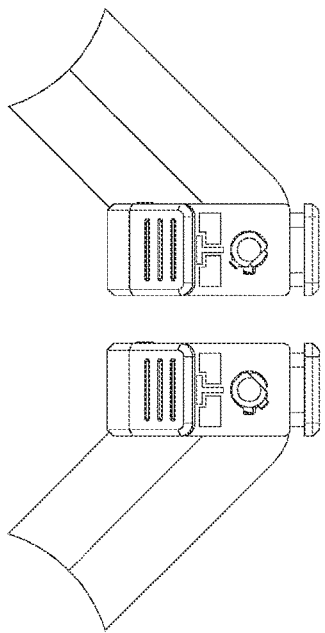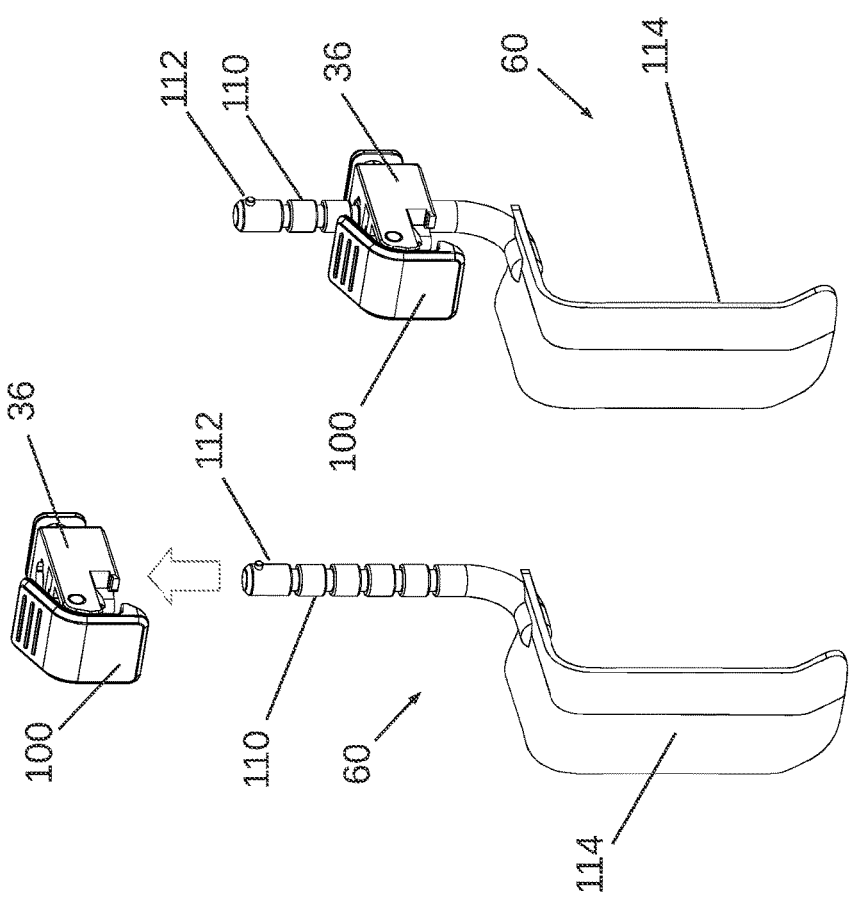

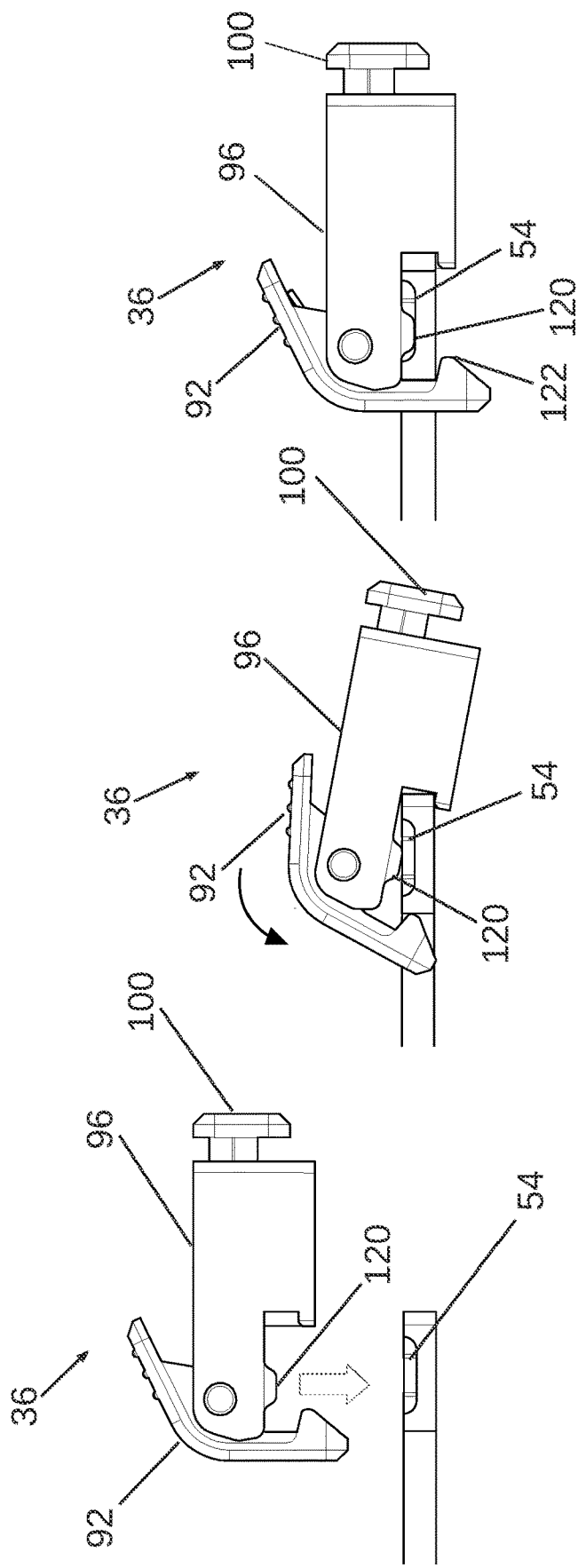

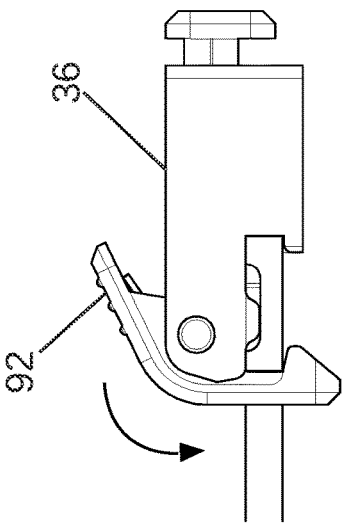
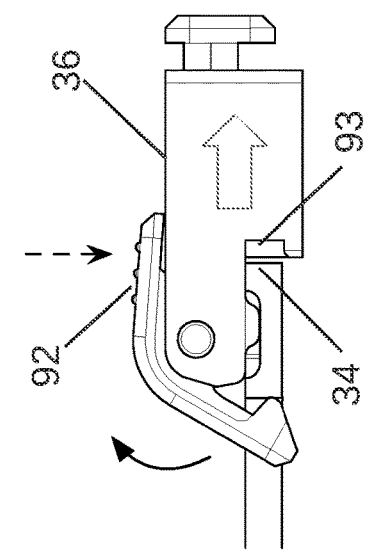
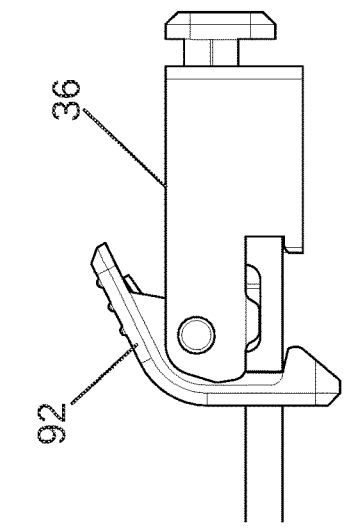
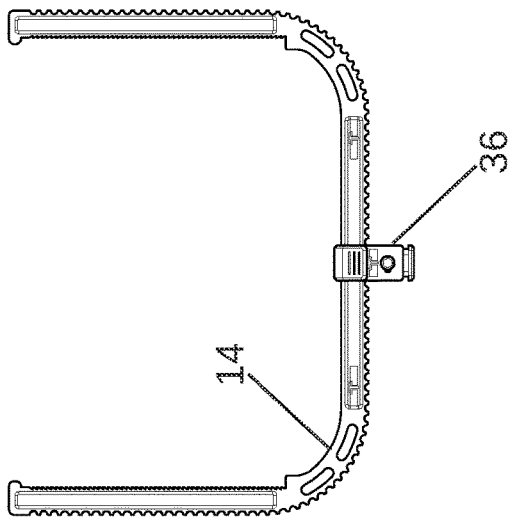
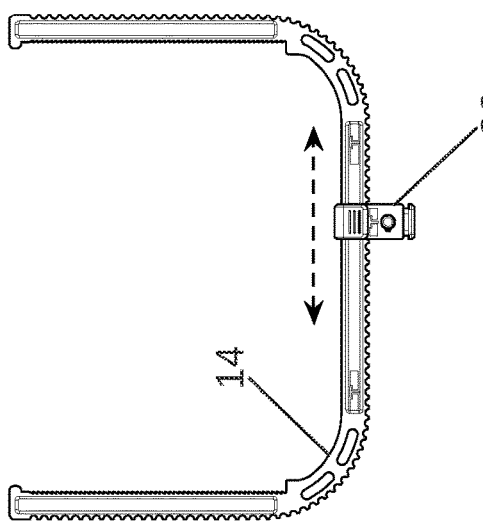
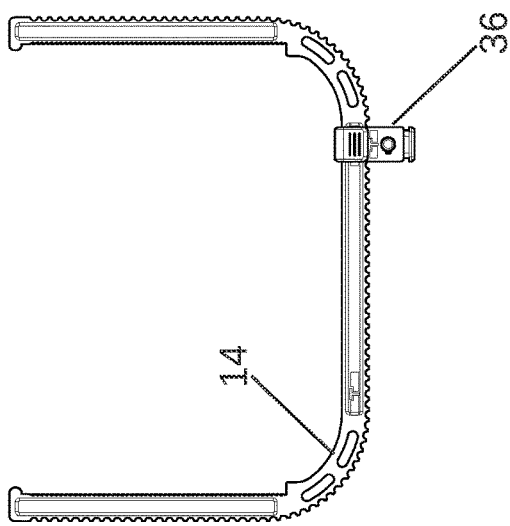
FIG. 28A
FIG. 28B
FIG. 28C

MID-EXPANSION

FULLY COLLAPSED

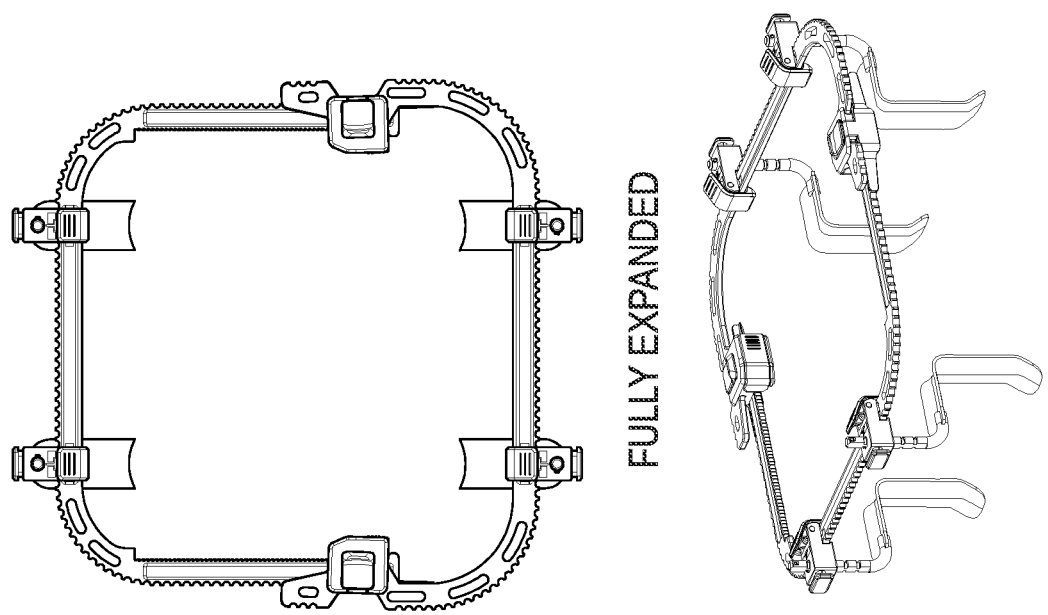

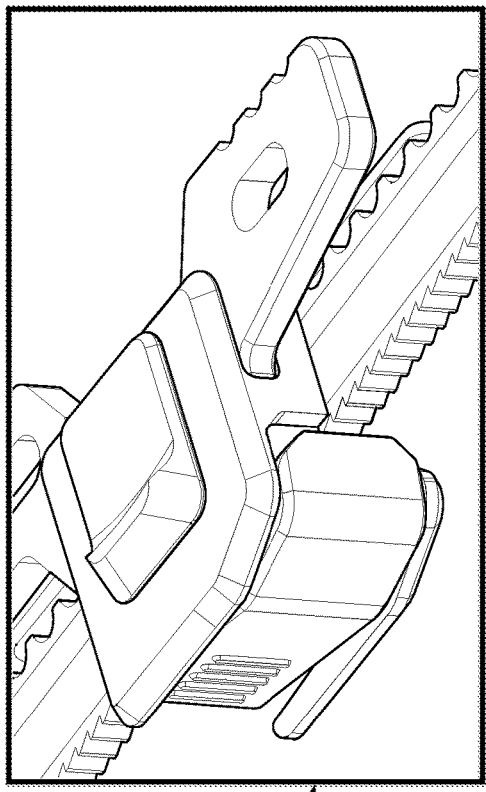
Ratchet button in "released" position; Required to collapse system.
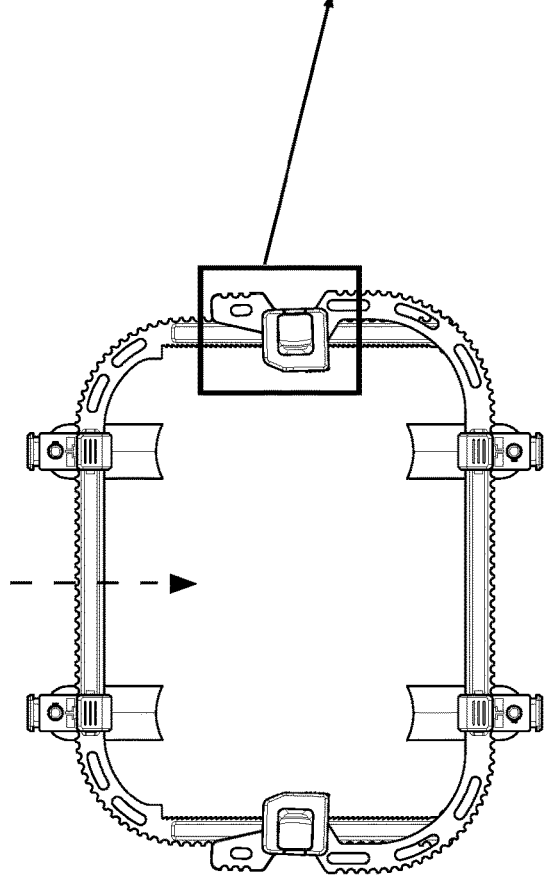
MID-EXPANDED
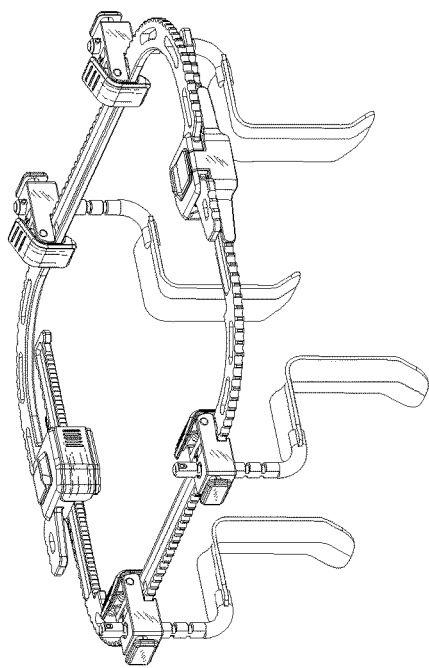
FIG. 30A

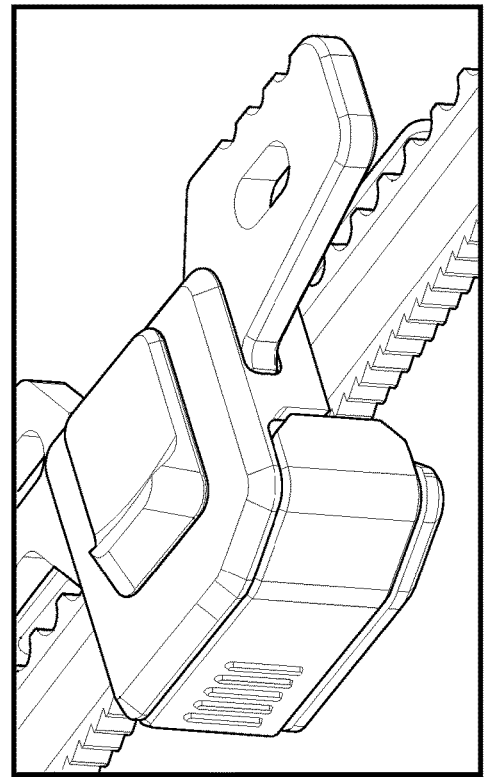
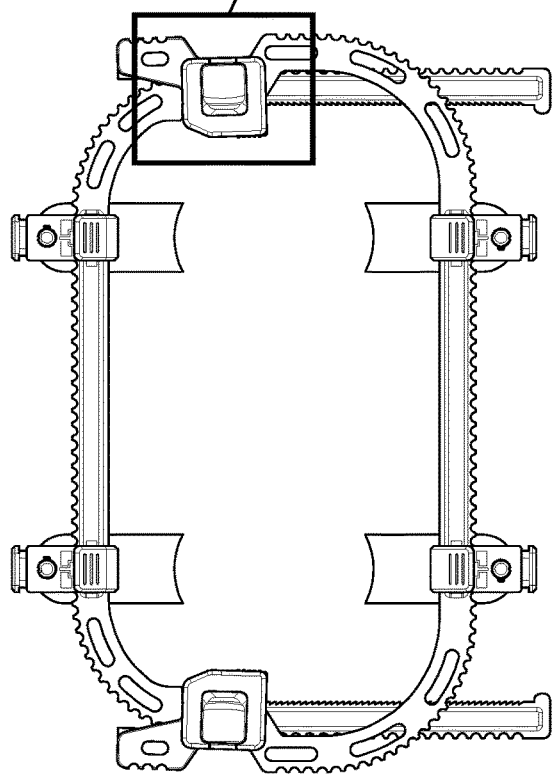
FULLY COLLAPSED
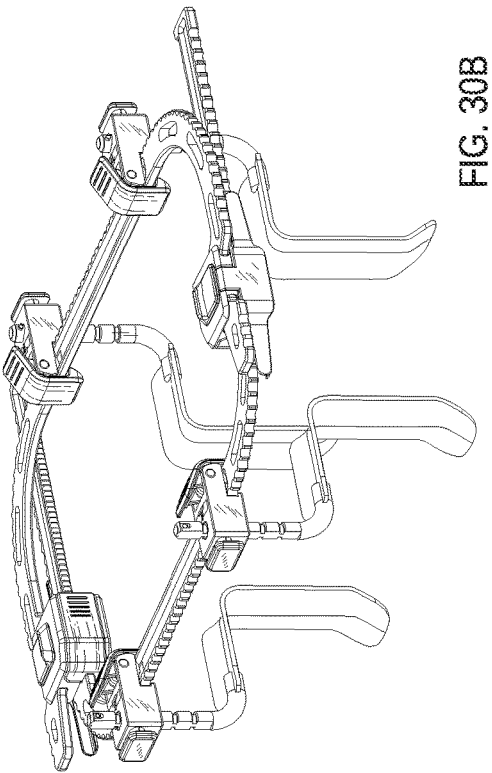
FIG. 30B
Ratchet button in "locked" position;

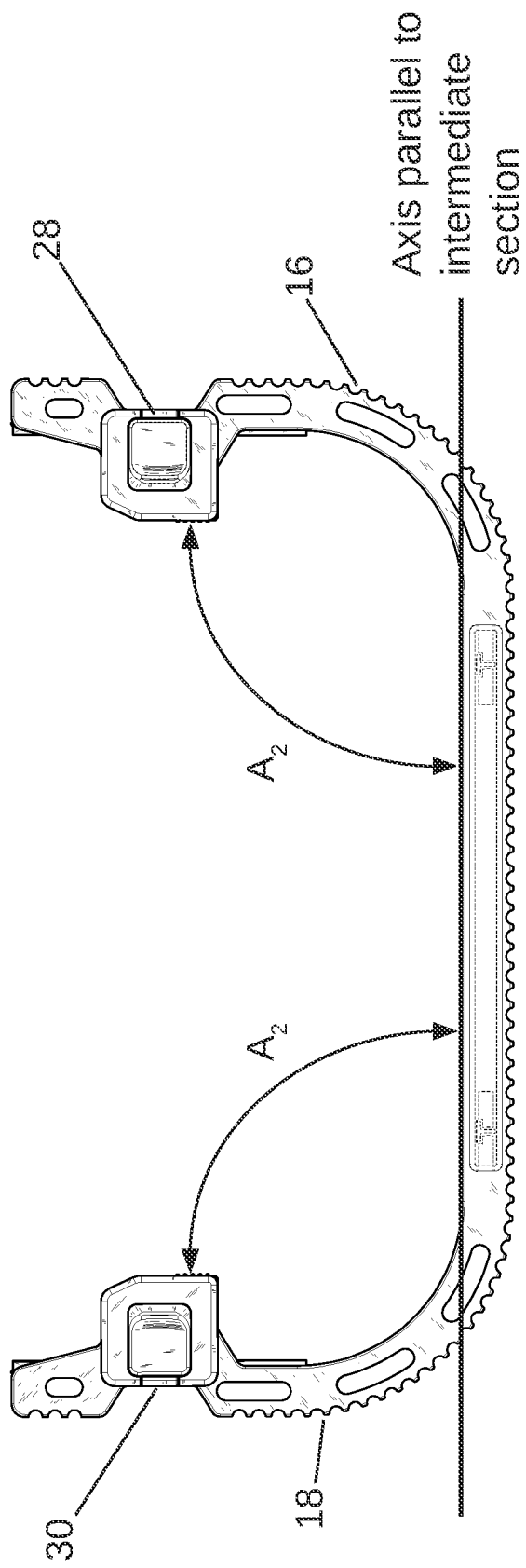
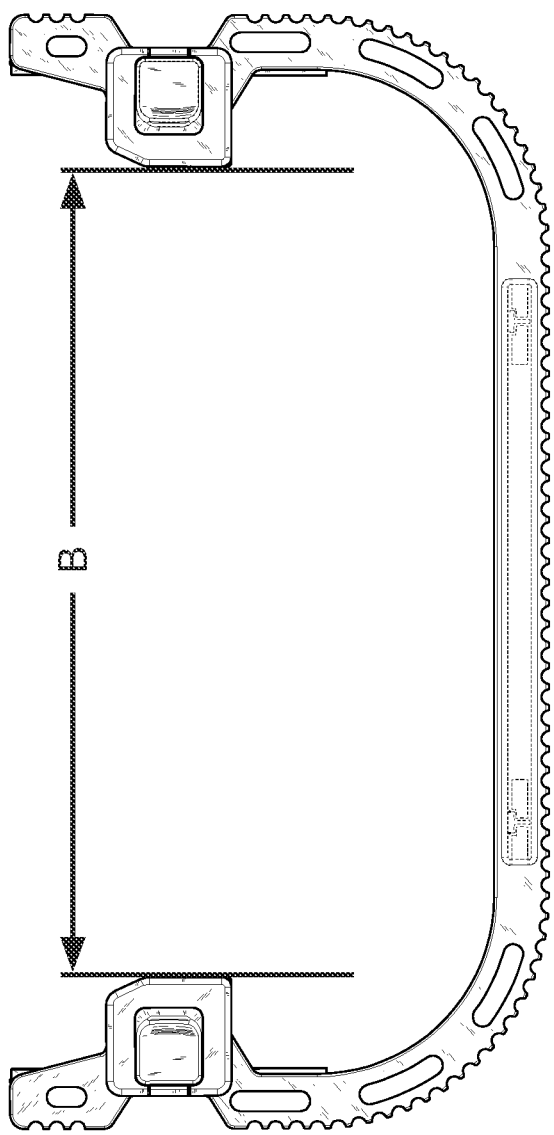
FIG. 34A
FIG. 34B

SURGICAL RETRACTOR

CROSS REFERENCE TO RELATED APPLICATIONS

This application is a 371 national stage entry of International Patent Application No. PCT/US2022/011044 which claims priority to U.S. Provisional Patent Application No. 63/133,408 filed Jan. 3, 2021, titled "Surgical Retractor", the disclosure of each of which is herein fully incorporated by reference.

FIELD

This application relates generally to surgical retractors and associated attachments and connectors.

BACKGROUND

This section is intended to provide a background or context to the invention that is recited in the claims. The description herein may include concepts that could be pursued but are not necessarily ones that have been previously conceived or pursued. Therefore, unless otherwise indicated herein, what is described in this section is not prior art to the description and claims in this application and is not admitted to be prior art by inclusion in this section.

Abdominal operations in both emergency and elective surgery settings require adequate exposure of abdominal contents in order for the surgeon to properly visualize areas of injury or disease. This is typically accomplished by the use of static metal retractors. Two of the most common retractor mechanisms in current use are the Balfour retractor and the Bookwalter retractor. Each of these retractors presents advantages and disadvantages in their design and use. The Balfour retractor consists of a frame with integrated metal blades on a ratchet system which, when engaged, retracts the abdominal wall laterally, thereby exposing the abdominal contents and allowing the surgeon to operate. The Bookwalter mechanism consists of a supporting frame attached to the operating table upon which a rigid non-adjustable metal ring is attached to which retractor blades are then attached individually.

The Balfour retractor is perhaps the most commonly utilized abdominal retractor due its simple design, ease of use, and rapid exposure of the abdomen, particularly in trauma and emergency surgery settings when time is of the essence. Since it does not require the attachment of a metal frame to the operating room bed, as with the Bookwalter retractor, valuable time is not wasted, and it can be quickly inserted after the abdominal incision is created.

Despite the Balfour retractor's prevalence in operating rooms and ease of utilization, there are several limitations to its use. For example, it provides inadequate abdominal exposure of large or obese patients. In larger or obese patients, the current design of the standard Balfour retractor often does not provide enough retraction to adequately expose the abdomen. The frame along which the retractor blades run is typically too short for larger or obese patients, resulting in suboptimal exposure and frequently necessitating conversion to another retractor system. Due to the Balfour retractor's inherently limited design, the surgical incision is only retracted along one axis (transverse), limiting overall exposure of the wound. An optional additional retractor blade (bladder blade) can be attached which only adds retraction in the inferior direction, typically resulting in suboptimal exposure requiring conversion to another retractor system.

The standard Balfour retractor does not provide an additional frame upon which to attach additional retractor blades except for a single bladder blade. This significantly limits the ability to retract additional incisional or abdominal contents compared to other retractor mechanisms, thereby limiting surgical exposure. Additionally, the Balfour retractor system commonly poses a significant problem during its use due to the unintentional movement and migration of the retractor blades along the edges of the surgical wound. The two retractor blades which provide lateral traction on the wound edges (or abdominal wall in abdominal operations) frequently unintentionally migrate to either the superior or inferior parts of the wound, causing rotation of the entire retractor mechanism, loss of wound edge retraction, and requiring either time-consuming repositioning of the retractor or conversion to another type of retractor system. This is particularly common in large or obese patients and in situations where the Balfour retractor system is significantly extended for use with larger wounds or surgical openings. In brief, the deficiencies of the Balfour retractor system are augmented when the system is scaled to larger wounds.

The Bookwalter retractor is typically the retractor system used when the Balfour retractor system is considered inadequate or ineffective. It consists of a supporting metal rod which is attached to a side rail on the operating room table by a non-sterile individual in the operating room after the patient is under anesthesia (the rail on the operating table is not considered part of the sterile operating field). A second metal arm is then attached to this supporting rod, and a rigid circular or oblong metal ring is then attached to the second metal arm. Once this is in place, individual retractor blades can then be attached, using the rigid ring for support.

Despite the popularity of the Bookwalter retractor it also presents several limitations. The Bookwalter retractor mechanism involves fixation to the operating room table which requires attachment by a non-sterile individual in the operating room. Occasionally this may cause concerns in maintenance of the sterile field, as the surgeon may need to place his hands below the sterile barrier in order to assist and properly place the retractor arm. In addition, the multiple arms which require setup before surgical retraction is achieved mandate a significant amount of time in instrument setup, rendering this system inadequate for emergency settings or operations when time is of the essence. The circumferential ring used in the Bookwalter system is not expandable and frequently limits the placement of additional retractors in both the longitudinal and transverse axes. In addition, the fixed sizes of the rings do not allow adjustment of retraction depending on the individual physical characteristics of each patient and various types and sizes of wounds or incisions. The Bookwalter system also requires frequent repositioning by the surgical team during its use. After the Bookwalter system is set up and attached to the bed frame, the ring system is thereby fixed in place and additional retractors are attached. However, as the operation progresses and surgical exposure requirements change, the system needs to be repositioned to place the static non-expandable ring into the correct location. This requires interruption of the operation, removal of the retractor blades, repositioning of the ring, and reattachment of the retractor blades, again requiring significant time. There is an existing need for additional retractor systems.

SUMMARY

In some embodiments, a surgical retractor assembly may include a first frame segment including a middle section disposed between a first end and a second end. The surgical retractor assembly may further include a second frame segment including an intermediate section and a pair of end sections projecting from the same side of the intermediate section, the pair of end sections maintaining a substantially parallel orientation with respect to each other, each of the pair of end sections including a top surface and a bottom surface. The surgical retractor assembly may further include a pair of connectors, the pair of connectors being configured for coupling the first frame segment to the second frame segment. Each of the pair of connectors may include a ratchet housing for connecting one of the pair of connectors to one of the ends of the first frame segment. A channel is formed within the ratchet housing, the channel being shaped to receive a top surface or a bottom surface of one of the end sections of the second frame segment. A ratchet fastener is configured for holding the one of the end sections of the second frame segment within said channel. Thus, for example, the surgical retractor assembly may comprise frame segments that may be vertically overlaid upon each other and coupled together. Once coupled together, the frame segments may define an adjustable frame that may be expanded or contracted so as to help visual a patient wound or incision. For example, in one preferred embodiment, the channels of the pair of connectors may be configured to receive the top surfaces of the end sections of the second frame segment when the pair of connectors are vertically overlaid on top of the second frame segment and lowered so that the end sections of the second frame segment are received within the channels. Notably, this allows the frame segments to be coupled together in certain situations where the first frame segment is already in use in a medical procedure and without requiring a surgeon to step or lean back from the surgical table.

In some embodiments, a surgical retractor assembly may include a first frame segment including a middle section disposed between a first end and a second end, and a second frame segment including an intermediate section and a pair of end sections projecting from the same side of the intermediate section, the pair of end sections maintaining a substantially parallel orientation with respect to each other, each of the pair of end sections including a top surface and a bottom surface. The surgical retractor assembly may further include a pair of connectors, the pair of connectors configured for coupling the first frame segment to the second frame segment in order to form a retractor frame, and at least one blade assembly. The at least one blade assembly may include a blade including a front blade face, the front blade face configured to be disposed adjacent a tissue wall of a wound or incision. The surgical retractor assembly my further include at least one blade block configured for mounting the at least one blade assembly on the retractor frame, the blade block being configured for selectively orienting the front blade face in the direction of the tissue wall. Accordingly, the surgical retractor assembly may be formed into a frame more easily in an emergency situation while avoiding inadvertent damage to the patient's tissues when a blade is incorrectly positioned away from the tissue wall.

In some embodiments, a surgical retractor assembly may include a first frame segment including a middle section disposed between a first end and a second end. The surgical retractor assembly may further include a second frame segment including an intermediate section and a pair of end sections projecting from the same side of the intermediate section, the pair of end sections maintaining a substantially parallel orientation with respect to each other, each of the pair of end sections including a top surface and a bottom surface. The surgical retractor assembly may further include a pair of connectors, the pair of connectors configured for coupling the first frame segment to the second frame segment in order to form a retractor frame. The first end of the first frame segment may be art of an extended substantially straight first end section, and the second end of the first frame segment being part of an extended substantially straight second end section. The first end section of the first frame segment and the second end section of the first frame segment extending from the same side of the middle section, the first end section and the second end section being outwardly canted away from each other at an angle suitable to reduce a risk of racking when expanding the retractor frame.

In some embodiments, a surgical retractor assembly may include a first frame segment, a second frame segment and a pair of connectors for connecting the first frame segment to the second frame segment during retractor frame assembly, the surgical retractor assembly comprising: said first frame segment, the first frame segment including an intermediate section, a first end section, and a second end section, the intermediate section disposed between the first end section and the second end section, the first and second end sections projecting from the same side of the first intermediate section; said second frame segment, the second frame segment including an intermediate section, a first end section, and a second end section, the intermediate section disposed between the first end section and the second end section, the first and second end sections projecting from the same side of the first intermediate section; and said pair of connectors including a first connector configured for coupling to the first end section of the first frame segment and a second connector configured for coupling to the second end section of the first frame segment; wherein each of the pair of connectors includes a channel configured for receiving an end section of the second frame segment when the end section and the channel are aligned about in parallel with each other and vertically overlaid.

BRIEF DESCRIPTION OF THE DRAWINGS

FIG. 8A shows an embodiment of a frame segment of a surgical retractor and showing connection between the segment and a connector or ratcheting subassembly.

FIG. 12 shows an embodiment of a surgical retractor kit.

FIG. 13A shows an embodiment of left and right ratchet subassemblies.

FIG. 13B shows a component view of the left-side ratchet subassembly shown in FIG. 13A.

FIG. 13C shows perspective views the left-side ratchet subassembly shown in FIG. 13A including a first view suitable for viewing the top side of the ratchet subassembly and a second view suitable for viewing the bottom side of the ratchet subassembly FIG. 14 is an illustration of an embodiment for joining two frame segments together.

FIG. 21 shows an embodiment of components used to construct a blade assembly.

FIG. 22 shows a blade assembly in a first orientation.

FIG. 23 shows a blade assembly in a second orientation.

FIG. 24A shows a blade block and blade assembly before joining the components.

FIG. 24B shows a blade assembly mounted to a blade block.

FIG. 25 shows a top down view of a blade assembly mounted to a blade block. FIG. 25 further shows an expanded view the blade assembly mounted to a blade block annotated with pertinent parts showing an embodiment for selectively limiting rotation of the blade assembly within the blade block.

FIG. 26A shows a blade assembly mounted to a blade block and rotated in a first orientation.

FIG. 26B shows a blade assembly mounted to a blade block and rotated in a second orientation.

FIG. 27A shows a blade block positioned for mounting to a frame or frame segment.

FIG. 27B shows a blade block during an intermediate stage in mounting the blade block to a frame or frame segment.

FIG. 27C shows a blade block mounted to a frame or frame segment.

FIG. 28A shows a blade block mounted to a frame segment in a first position.

FIG. 28B shows the blade block of FIG. 28A actuated so as to move along the frame segment shown in FIG. 28A.

FIG. 28C shows the blade block of FIG. 28A locked in a second position along the frame segment shown in FIG. 28A.

FIG. 29C shows each of a top plan and a perspective view of an assembled frame in a fully-expanded configuration.

FIG. 30A shows each of a top plan and a perspective view of an assembled frame in a mid-expanded configuration and a ratchet button in a position suitable for collapsing the frame.

FIG. 30B shows each of a top plan and a perspective view of an assembled frame in a fully-collapsed configuration and a ratchet button in a locked position.

FIG. 34A-C show embodiments of a frame segment wherein the end sections of the frame segment are tilted or canted or where a connector includes a channel angled with respect to a connector housing.

DETAILED DESCRIPTION

Figure 1:
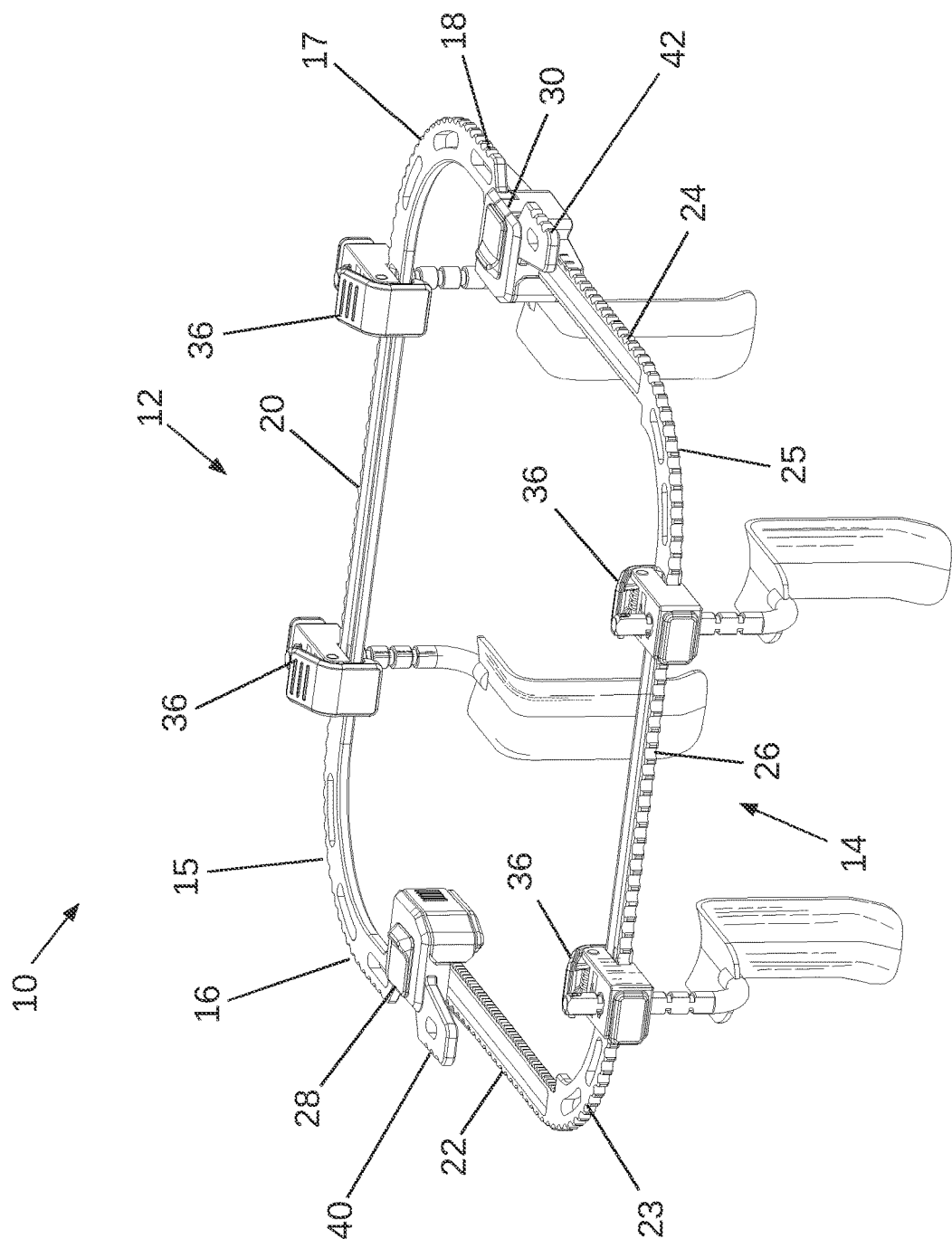
FIG. 1 is a perspective view of an embodiment of a surgical retractor assembled and shown in an expanded configuration.

The following terms as used herein should be understood to have the indicated meanings unless the context requires otherwise.

When an item is introduced by "a" or "an," it should be understood to mean one or more of that item.

"Comprises" means includes but not limited to.

"Comprising" means including but is not limited to.

"Having" means including but not limited to.

"Right" and "left" references are from a perspective of a patient lying face up and oriented so as to expose the patient's abdominal cavity.

This disclosure is directed to medical retractors, associated segments or arms of a retractor frame, attachments used with medical retractors, and related methods of making and using medical retractors. Attachment of the retractors described herein to an operating table or other support is not necessary, but can be an option for some embodiments, and therefore use of the retractors does not require involvement of any non-sterile member of the operating team or place the retractor in contact with any supporting structure that extends outside of the sterile field surrounding a surgical opening or wound. Thus, the retractors are less prone to contamination and more likely to remain sterile during retractor setup and use. The lack of a required obtrusive fixed metal frame supporting the retractor further allows the surgeon increased mobility and positioning at the sides of a patient during an operation. Furthermore, in contrast to some other retractors that might be used without an obtrusive metal frame, the retractors described herein pose minimal risk of unintentional movement and migration of the retractor blades along the edges of the surgical wound, thus solving key problems with other retractors in the prior art.

The retractors described herein are further configured for simple and rapid deployment so that they can be applied to emergency and time sensitive situations. For example, in some situations, the retractors may be installed during an active medical procedure, such as by making use of one frame segment of a pair of frame segments (e.g., to retract tissue so as to expose a surgical opening) and coupling another frame segment to the in-use frame segment without interrupting an ongoing surgical action. Specific features of the retractors, including, but not limited to the type of connectors used, relative sizes and shape of the frame segments, and configuration of associated blade blocks may help to facilitate use of the retractor in this way.

For example, a retractor may be assembled using a pair of frame segments by positioning the ends of one frame segment above the ends of another frame segment so that the respective ends of the two frame segments are aligned about in parallel with each other but offset in different vertical planes and then lowering one frame segment on another so as to engage the segments together using one or more connectors, such as snap-fit connectors, for example. This makes it easy to assemble the frame even in situations where one of the frame segments may need to be positioned underneath one or more arms of a surgeon without interfering with an ongoing surgical action. For example, one frame segment may be fitted with one or more blades disposed so that it may be used to grasp a free end of a wound or incision from a side that is located away from a surgeon (e.g., on an opposite side of a surgical table from where the surgeon is standing). The one or more blades may be used to pull back tissue so as to assist the surgeon in reaching into the wound or incision so that the surgeon may perform a medical action such as clamping an artery so as to help prevent bleeding, for example. The other frame segment of the pair of frame segments may then be positioned under one or both arms of the surgeon without disrupting the surgeon, and the two frame segments engaged so as to create a working frame.

Figure 16:
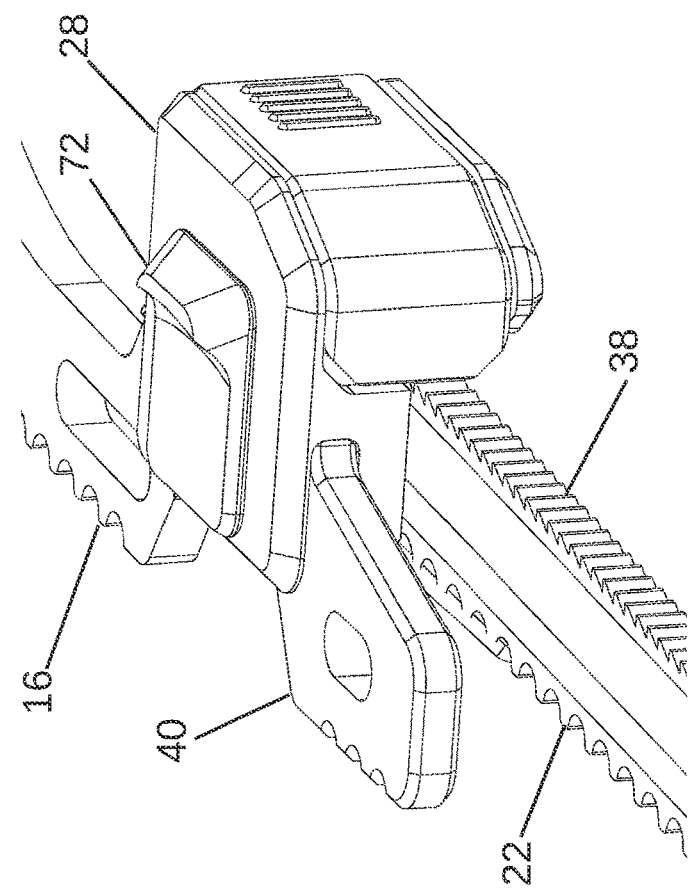
FIG. 16 shows an expanded view of ends of the two frame segments shown in FIG. 14 after the two frame segments are joined together.
Figure 15:
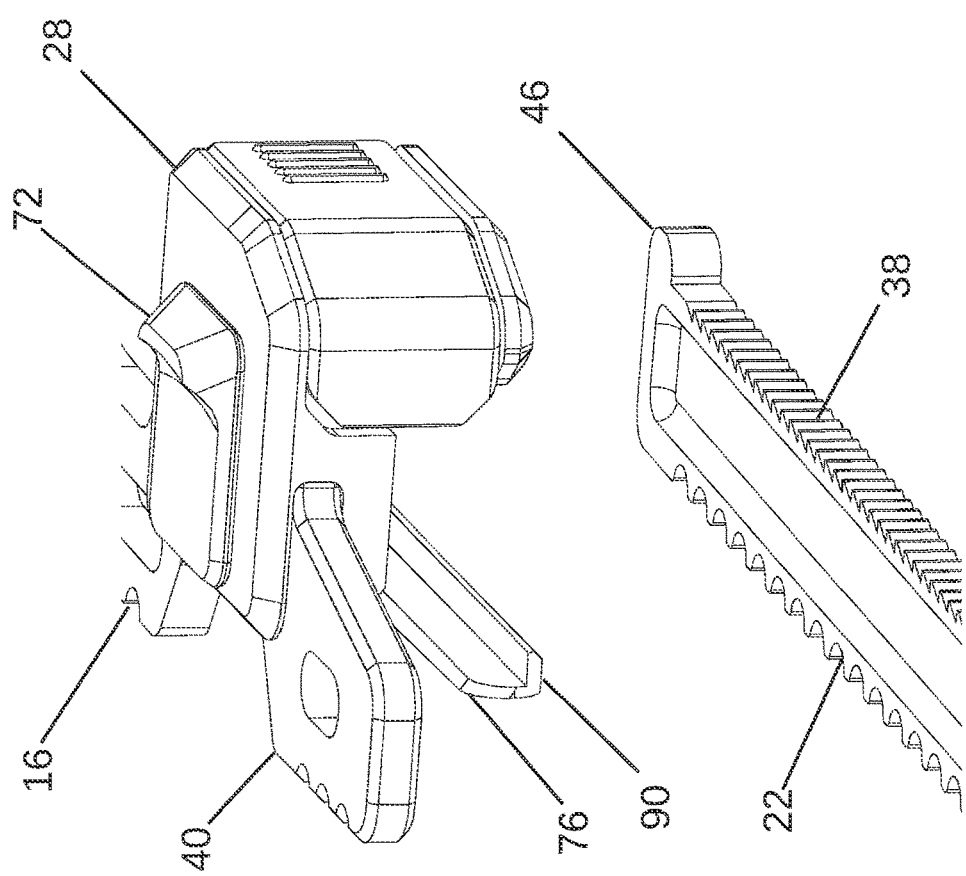
FIG. 15 shows an expanded view of ends of the two frame segments shown in FIG. 14 before the two frame segments are joined together.

It should be appreciated that, in this design, as also explained in relation to FIGS. 14-16, the frame segment that is positioned underneath the one or more arms of the surgeon need not be positioned adjacent the other frame segment in an end-to-end style for engagement (i.e., with the terminal ends of each frame segment aligned about in the same vertical plane so that the ends of each frame segment may be passed through one or more holes or lumens in a connector) as is the case in some other prior art retractors. Notably, assembly of the retractor in this way demands less room underneath the outstretched arms of the surgeon than does this alternative end-to-end style of attachment. In some embodiments, the width of at least one of the frame segments may further be selected to further aid in retractor assembly. For example, in some embodiments, the frame segment that is extended underneath the arms of the surgeon may be characterized by a width that is lesser than the other frame segment. Once the frame segments are connected so as to form the frame, the frame may be adjusted. For example, adjustment of the frame may be accomplished using a ratcheting or other mechanism so that end sections of the two frames move over each other with the end sections aligned in a substantially parallel relationship to each other.

The retractor blades described herein may sometimes be pre-installed on either or both of the frame segments. That is, the retractor blades may sometimes be mounted on frame segments before the frame segments are joined together. For example, one or more blade blocks or other attachments may be coupled to frame segments so that the frame segments may receive one or more retractor blades. Advantageously, the retractor blades may be held within the one or more blade blocks in a way so that they may be rotatably adjusted so as to grasp the walls of an incision or wound at an appropriate angle such as a desired angle to provide proper tension to hold the walls of a wound or incision site to aid in visualization. However, the blades may be selectively limited in rotation so that they are automatically oriented at least generally in a proper orientation during retractor assembly, thereby facilitating rapid use of the device. For example, as further described in greater detail in relation to FIG. 25, a blade block may include a rib or other feature (e.g., a mechanical stop) so as to selectively limit rotation of a retractor blade post within a blade block hole. The stop may automatically orient a blade so as to prevent the blade from rotating so that a front side face of the blade is not properly facing the tissue wall upon which it is meant to engage. Accordingly, the surgeon or surgical staff may not have to spend time manually adjusting the position or orientation of the blade during retractor assembly. Inadvertent damage to adjacent tissue near a wound or incision site, such as may sometimes occur if a blade is rotated incorrectly during insertion, may also be avoided. Further, in some embodiments, a mechanical stop or rib may help to prevent changes in angle of the blade that may accompany inadvertent migration of the retractor about the wound. Thus, a rib or stop may be shaped so as to minimize risk of damage to tissue during initial setup or assembly of a retractor, shaped to help prevent inadvertent migration of the retractor about the edges of the wound during a surgical procedure, or both.

The retractors described herein further include specific modifications to substantially eliminate risk of racking or jamming during retractor assembly, including when expanding or contracting the frame. For example, in some embodiments, connectors may be rigidly attached to one member of a pair of frame segments used to form the frame. A connector may, for example, be welded of otherwise fixed to one of the frame segments so as to substantially eliminate any movement between the connector and that frame segment. This stabilization may help to reduce misalignment between the frame segments when expanding or contracting the frame. In some embodiments, frame segments may be received within a channel of a connector, wherein the channel and frame segment may include one or more features complementary in shape so as to help guide seating of the frame segment within the channel and to guide sliding movement therebetween so as to substantially eliminate a risk of racking. For example, the channel may include a groove formed therein and the frame segment may include a ridge shaped to sit within the groove, or vice versa. In some embodiments, this channel may be extended in width so as to increase a surface area of contact between the channel and the frame segment received therein. Further, in some embodiments, frame segments may be shaped with an outward slope or cant so as to further help substantially eliminate a risk of racking.

In some embodiments, the retractor may be made of a lightweight yet strong material for easy handling by personnel operating within the sterile field, e.g., surgeons and operating room technicians. Notably, the lighter the material, the less tension that must be applied to the incision to counteract the weight of the retractor so as to help keep the retractor from inadvertently sinking downward into a wound or surgical opening of a patient. In some embodiments, retractors herein may comprise or be made from titanium, carbon fiber, carbon fiber reinforced thermoplastics or thermoplastics. For example, thermoplastic materials suitable for some embodiments of the retractors described herein include polycarbonate, polypropylene, polyethylene. In some embodiments, one or more openings, holes, or indentations may be configured within a frame segment. The openings or holes may provide a distinctive shape to the segments. The openings, holes, or indentations may further reduce an amount of material used in making a frame segment and reduce a frame segment weight. These and other advantageous features which may be included in some of the various embodiments herein are further described below.

Figure 2:
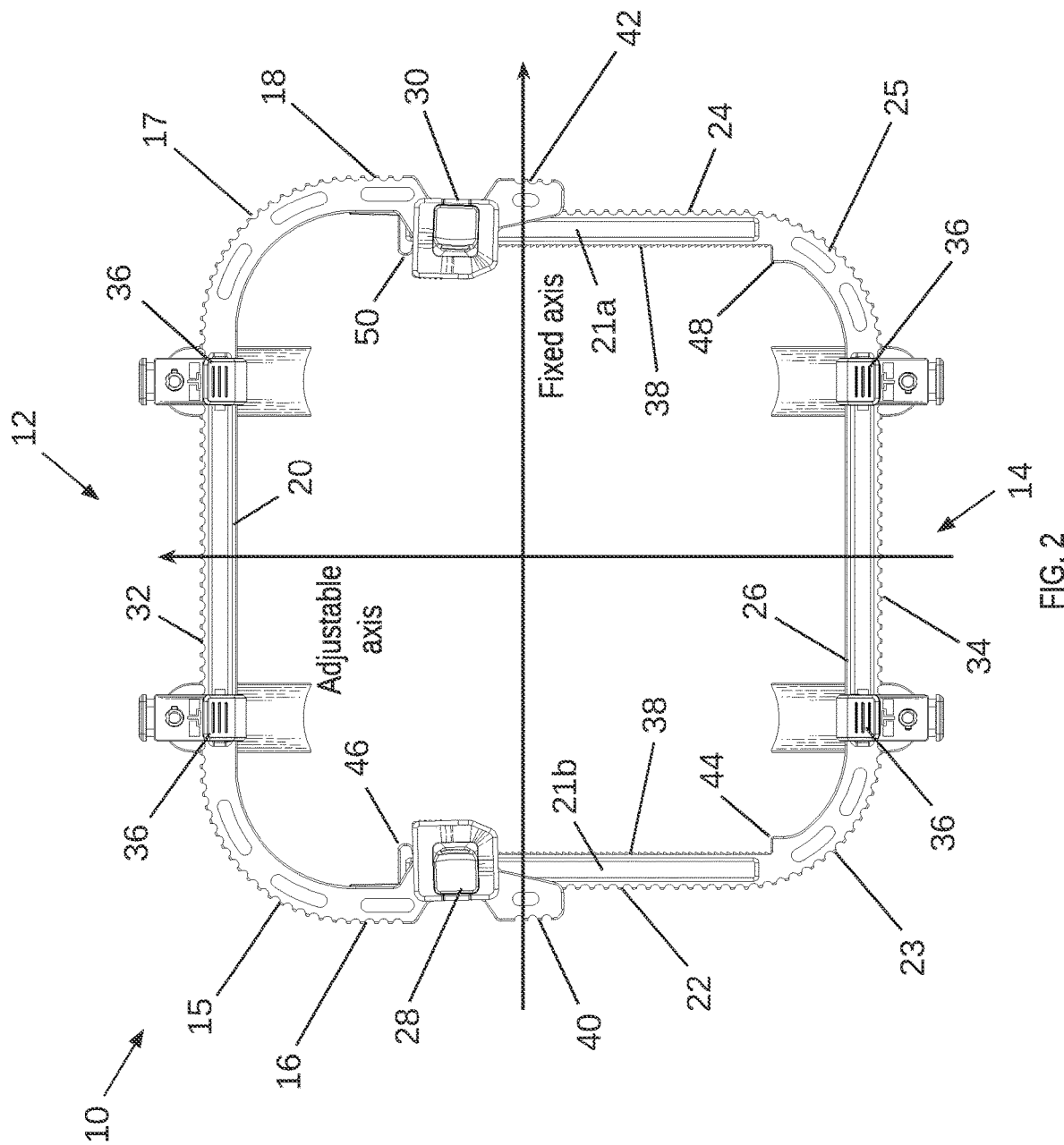
FIG. 2 is a top plan view of the surgical retractor of FIG. 1 assembled and shown in an expanded configuration.
Figure 3:
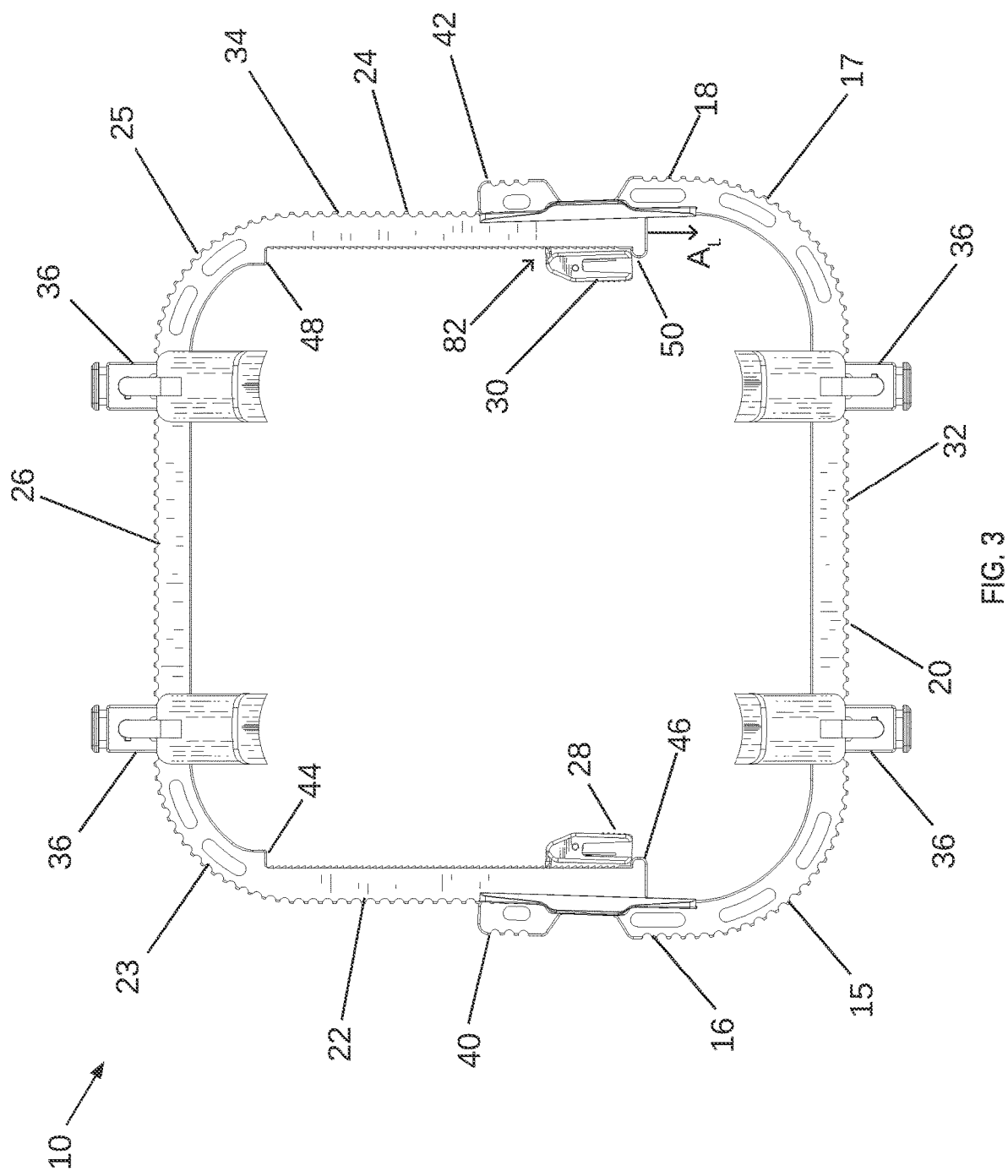
FIG. 3 is a bottom plan view of the surgical retractor of FIG. 1 assembled and shown in an expanded configuration.
Figure 4:
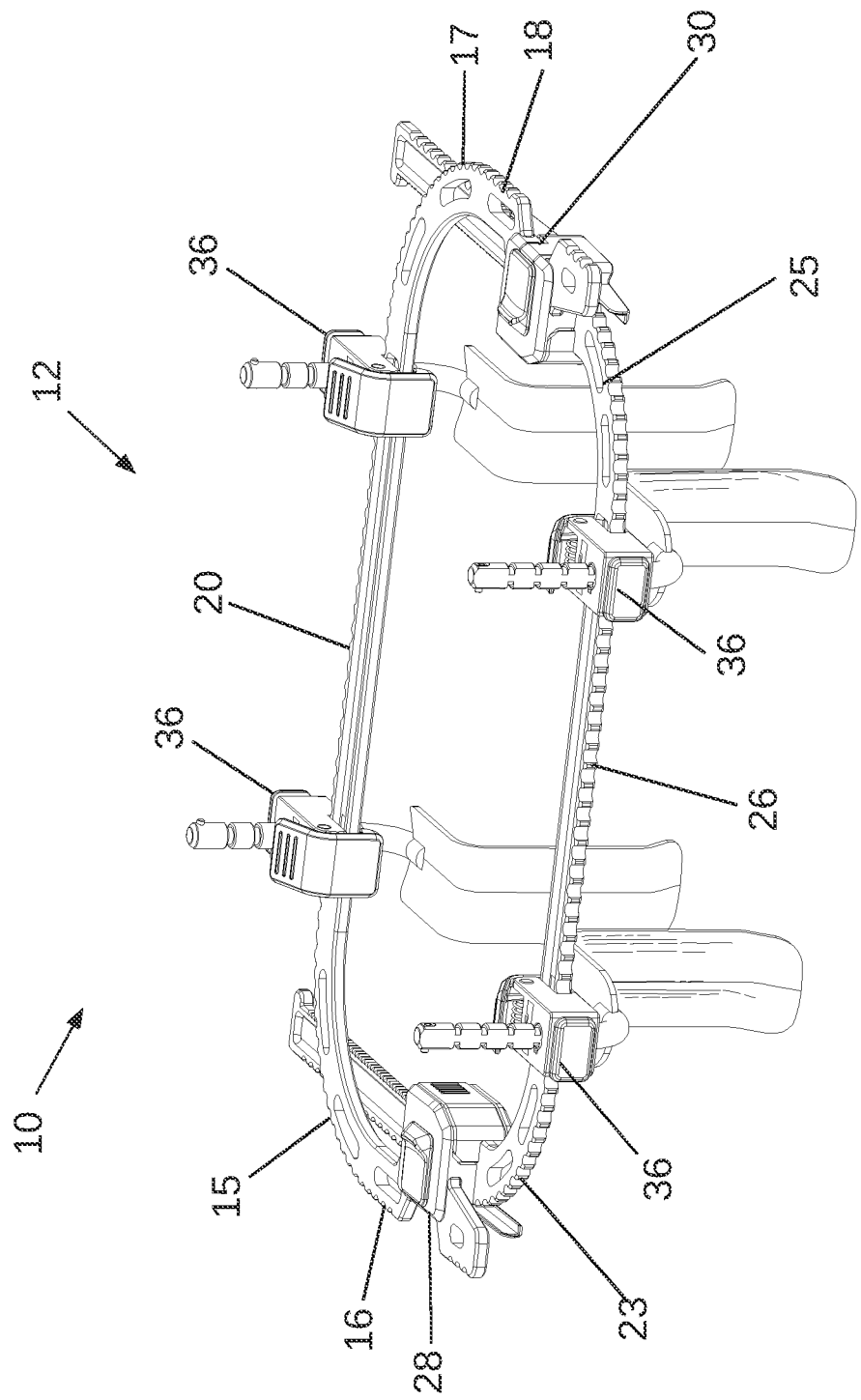
FIG. 4 is a perspective view of the surgical retractor of FIG. 1 assembled and in a collapsed configuration.

For example, various embodiments of a retractor 10 are described in relation to FIGS. 1-4, which show the surgical retractor 10 assembled as it might be when used to visualize a patient incision or wound and in an expanded state (FIGS. 1-3) and in a collapsed state (FIG. 4). The retractor 10 may comprise a frame including at least two frame segments 12, 14. For example, a first frame segment 12 may comprise each of a first end section 16 and a second end section 18, the two end sections 16, 18 being connected through a middle or intermediate section 20 and curved sections 15, 17. A second frame segment 14 may comprise each of a first end section 22 and a second end section 24 connected through a middle or intermediate section 26 and curved sections 23, 25. When the retractor 10 is in an assembled configuration, the first frame segment 12 may be coupled to the second frame segment 14 so as to define an adjustable frame. In assembling the frame, a first connector 28 may be used to join end section 16 of the first segment 12 with end section 22 of the second segment 14. Likewise, a second connector 30 may be used to join end section 18 of the first segment 12 with the end section 24 of the second frame segment 14.

For example, in some embodiments, the connectors 28, 30 may each include a channel 82 (shown in FIG. 13C), the channel being sized so as to receive one of the end sections 22, 24 when the channel 82 is aligned about in parallel with a longitudinal axis ($A_L$) of the end section. For example, as best shown in FIG. 2 and FIG. 3, a longitudinal axis ($A_L$) of the end section 24 is shown aligned with the channel 82 (the channel is hidden from view in FIG. 3, but generally positioned as shown by the associated arrow). The channel 82 may, for example, be formed at least in part within a housing of a connector 28, 30 (as best shown in FIG. 13C, for example) and shaped to receive a top surface 21a on the end section 24 of frame segment 14. A user may, for example, actuate one or more buttons or locks on a connector 28, 30 so as to provide access to the channel so that an end section 22, 24 may become inserted and nested therein. Upon receiving of an end section 22, 24 within the channel, the connector may sometimes snap in place or otherwise provide an audible or tactile indication of the connection. Thus, connectors herein may allow the segments 12, 14 to be snap fitted together. An audible or tactile indication of connection may, for example, be particularly useful in situations wherein a member of a surgical team is tasked with engaging one frame segment with another in situations wherein a surgeon is already engaged in a surgical procedure.

Notably, this may be done when a connector 28, 30 (e.g., a connector which may already be coupled to the first frame segment 12) is vertically overlaid upon an end section 22, 24 of the second segment 14 so as to receive a top surface 21a, 21b and the segments 12, 14 snap fitted together. This procedure, may, for example, be contrasted with other procedures, such as those which may require the terminal end of an arm to be threaded through separate holes or lumens in the connector (e.g., an end-to-end style for engagement of the frame segments). Such an end-to-end style of engagement may require more room than might be available when a surgeon is already engaged in a medical procedure. For example, that style of engagement may require an attending surgeon to step or lean away from the surgical table during frame assembly so that space is made available to position a frame segment so that the terminal end of the frame segment may be aligned with an opening in the connector. In some embodiments, the width of at least one of the frame segments may further be selected to further aid in frame assembly. Once coupled together, the connector 28, 30 may slidably move across the end section 22, 24 during frame adjustment and held in a selected configuration using a ratcheting mechanism. Generally, the connectors 28, 30 may engage an end section 22, 24 anywhere along about the entire length of the end sections 22, 24 so that engagement of the segments is again simplified and may be done quickly. Thus, the connectors 28, 30 may be specifically adapted for quickly connecting the frame segments 12, 14 together, and the widths of the segments 12, 14 (e.g., as may sometimes be embodied with a relatively extended end section 22, 24 length of frame segment 14 and shorter end sections 16, 18 of frame segment 12) configured to further aid a user in frame assembly.

The retractor 10 may be characterized as defining a frame comprising the two frame segments 12, 14 when the segments 12, 14 are coupled together. The frame may define an enclosed region configured to provide access to a wound or incision site. The frame may be described as having a perimeter which may be adjusted so as to size the frame as may be suited for a given surgery. For example, the frame shown in FIGS. 1-4 may define an approximately rectangular shape including an adjustable axis and a fixed axis. Where a frame includes an adjustable axis and a fixed axis, reference may be made to the length and width of the frame. The length of the frame may be characterized as the distance along the fixed axis. The width of the frame may be characterized as the distance along the adjustable axis. Thus, in this characterization the width of a frame may sometimes be greater in extent or lesser in extent than the length of the frame depending, for example, on whether the frame is in in a collapsed or an expanded state. As used herein, a substantially rectangular shape frame does not preclude curved edges at the corners of the frame.

Each of the first frame segment 12 and the second frame segment 14 may have teeth along one or more edges, and/or ridges or grooves along one or more faces. For example, with reference to FIG. 2 and FIG. 3, the first frame segment 12 may have teeth 32 on an outer edge thereof. Likewise, teeth 34 may be provided on an outer edge of the second frame segment 14. In some embodiments, teeth 32, 34 may be provided on an inner edge of the frame segments 12, 14 or ridges or grooves may be included on one or more faces of the frame segments 12, 14. One or more blade blocks 36 or other attachments may be adjustably positioned along the frame segments 12, 14. For example, blade blocks 36 may be configured to move along the teeth 32, 34 in a ratcheting mechanism or the blade blocks 36 may be disengaged from the teeth 32, 34 so that the blade blocks 32 may slide along the frame. In other embodiments, as opposed to moving on teeth 32, 34, blade blocks may move across groove, ridges, or another suitable structure so as to allow for adjustable positioning.

Frame segments 12, 14 can be connected to each other using the connectors 28, 30. For example, connectors 28, 30 may comprise a ratchet mechanism that interacts with ratchet teeth 38 to adjustably secure frame segments 12, 14 in a selected position and allowing for expansion and collapsing of the frame. In some embodiments, a directional ratchet may allow a part of the frame to move in one direction that results in expansion of the frame and resists or does not allow movement in the opposite direction, i.e., frame collapsing or contraction. In some embodiments, one or more of the connectors 28, 30 may be configured so that a retractor blade or other attachment may be positioned thereon or on an adjacent wing section. For example, the connector 28 may include a wing 40, the wing 40 suitably shaped so as to accept a standard Bookwalter style attachment or other attachment. For example, as shown in FIGS. 34A-B (which shows left-side connector 30 and the associated wing 42), a Bookwalter style attachment 35 may be positioned on the wing 42. The wing 42 may be shaped so that a vertical height of the wing 42 in relation to the top of the frame connector 30 allows the user to access one or more Bookwalter adjustment levers 31 on the attachment 35 even if the attachment 35 is disposed adjacent "face-to-face" with the connector 30. Accordingly, a Bookwalter style blade 33 or other attachment may be flexibly positioned around the frame including, for example, at the mid-point of any side of the frame, including adjustable sides of the frame. Notably, the ability to position an attachment at the mid-point position of the side of the frame may be particularly useful because this position may be used to help provide adequate visualization of internal tissue, particularly in larger incisions that may be useful for surgeries performed on large or obese patients.

It should be noted that for some frames in some states of expansion, the connectors 28, 30 may be positioned near or at the mid-point of the frame. Some embodiments herein that include a wing 40, 42 may allow a user to still position a blade or other attachment at about the midpoint of the frame by providing flexibility to connect the attachment either along the wing 40, 42 or at some other position on the frame, such as alternative positions A, B shown in FIG. 34A. That is, depending on a required level of frame expansion a user may move a blade to either of position A or position B so that a blade may always be placed at about the mid-point of the frame.

In some embodiments, the wing 40 may be shaped so that an attachment may be placed thereon and a separate blade block 36 or other attachment may be mounted near or underneath the wing 40 on the underlying section 22 of frame segment 14. In some embodiments, to accommodate placement of one attachment near the wing attachment or even directly underneath the wing attachment, the wing 40 may be vertically offset from the end section 22. For example, at least a portion of the wing 40 may be angled so as to position the wing 40 above the underlying section 22 or the wing 40 may extend from the connector 28 at a height that is offset from the underlying section 22. This arrangement may be particularly advantageous for complex surgical procedures where multiple attachments may be needed to properly visualize tissue, illuminate tissue or perform some other function. Likewise, the connector 30 may include a similar wing 42 configured to engage an attachment. In some embodiments, the connectors 28, 30 may be connected to frame segment 12 using a frame that does not include a wing. In some embodiments, teeth 32, 34 may extend substantially around the full length of the frame, and the fame may be configured so that one or more attachments may be mounted substantially throughout the length of the frame. Embodiments wherein a plurality of blade blocks 36 or other attachments may be positioned on any given side of the frame may be particularly useful in sizing the retractor 10 for use with large or obese individuals.

In some embodiments, either or both of the frame segments 12, 14 may have one or more expansion or contraction stops. A stop may, for example, be in the form of a ridge, groove, screw, pin, hole, or elevated material that can contact or engage a connector 28, 30 to stop the movement of a frame segment through the connector 28, 30. Accordingly, inadvertent disassembly of the retractor may be prevented. For example, the second frame segment 14 may comprise expansion stops 46, 50. The second frame segment may further include contraction stops 44, 48.

Figure 5:
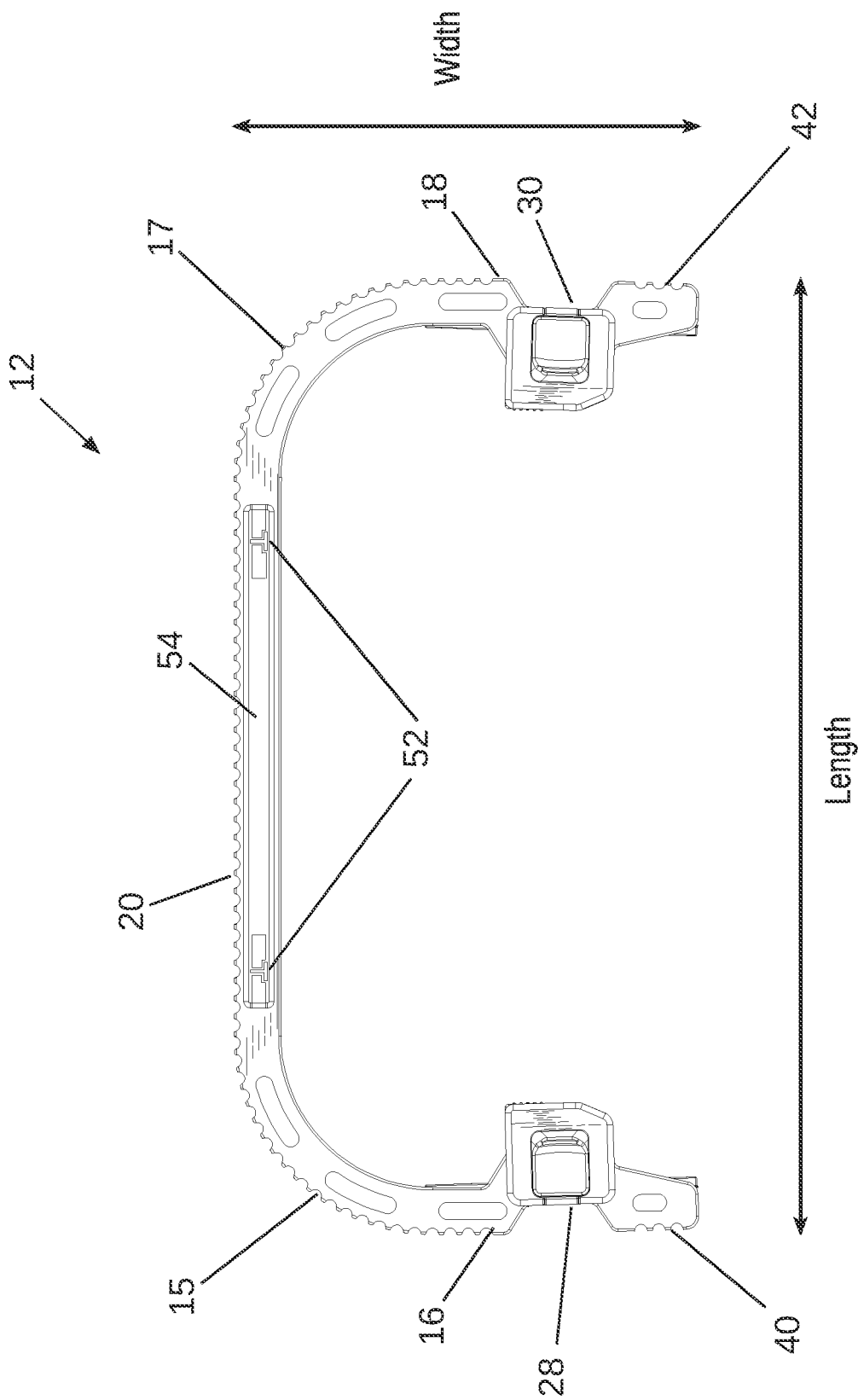
FIG. 5 is a top plan view of an embodiment of a segment of a surgical retractor and a pair of connectors attached thereto.
Figure 6:
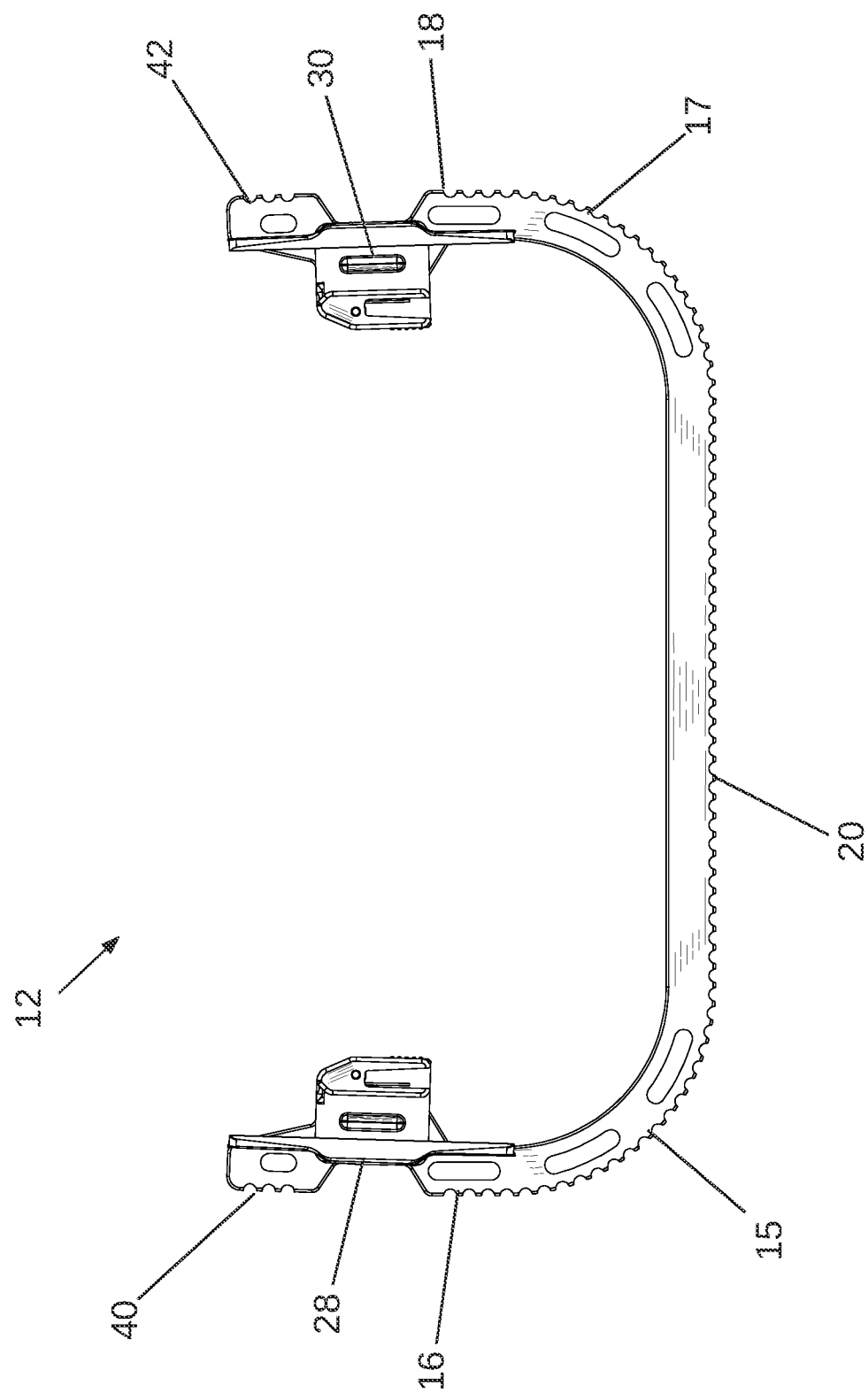
FIG. 6 is a bottom plan view of an embodiment of a segment of a surgical retractor and a pair of connectors attached thereto.
Figure 7:
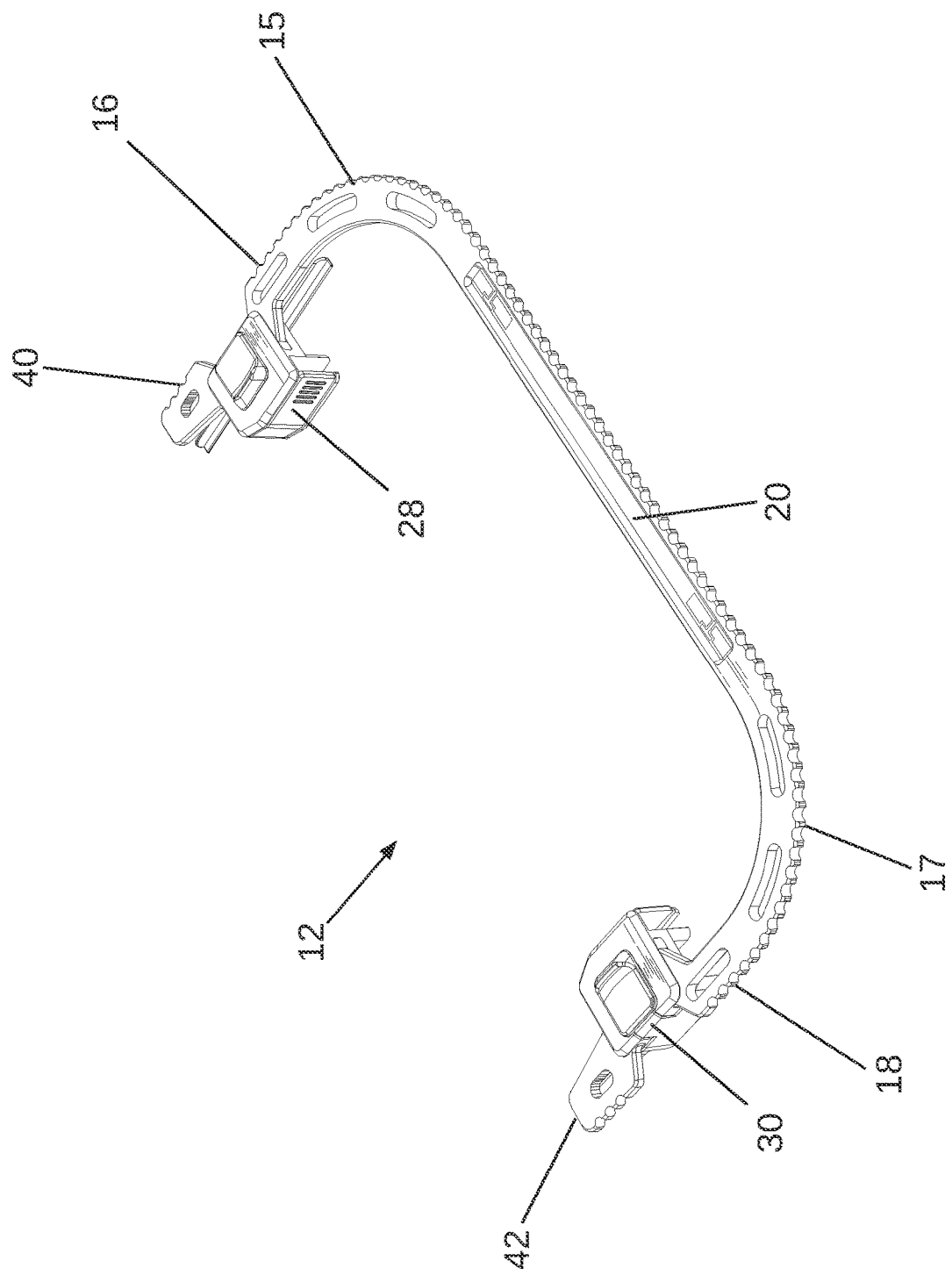
FIG. 7 is a perspective view of an embodiment of a segment of a surgical retractor and a pair of connectors attached thereto.

Various embodiments of a first segment 12 are further described in relation to FIGS. 5-7, which show the first segment 12, a pair of connectors 28, 30 attached thereto, and including wings 40, 42. As shown in FIG. 5, the first segment 12 may be generally "C" shaped with intermediate section 20 disposed between the two end sections 16, 18. The two end sections 16, 18 projecting from the same side of the intermediate section 20 and extending so that the two end sections 16, 18 are substantially parallel to each other. In some embodiments, the two end sections 16, 18 may be slightly tilted away from each other, such as at an angle of less than about 1.5 degrees. The term "substantially parallel" as used herein does not preclude the end sections from being purposefully canted away from each other at such small angles which as further described herein may sometimes be used to reduce risk of racking when expanding or contracting the retractor frame. For example, even with this small angle the end sections of each of the frame segments 12, 14 are still designed to move with respect to each other and to maintain a substantially parallel relationship to each other when expanding or contracting the frame.

The first segment 12 may include one or more markings or visual indicators 52 for suggested placement of blade blocks 36. For example, the visual indicators 52 may be spaced apart a recommended distance so that blade blocks 36 coupled thereto may work with corresponding blade blocks 36 on second frame segment 14 so that a surgical wound is stabilized in such a way to prevent unintentional movement and migration of retractor blades along the edges of the surgical wound. However, the retractor 10 may allow a user to position a blade block 36 at other positions along the frame segment 12. For example, in some embodiments, a central groove 54 may be provided on a top side of the first segment 12, the groove 54 assisting in positioning and movement of blade blocks 36. The visual indictors 52 and/or groove 54 may further help to identify a proper orientation for the frame segment 12. This may prevent a user from inadvertently trying to assemble the frame in an incorrect orientation. The first segment 12 may include each of a first end section 16 and a second end section 18, the two end sections 16, 18 being connected through a middle or intermediate section 20 and curved sections 15, 17. The curved sections 15, 17 may be defined by a degree or level of curvature suitable to transition from the intermediate section 20 to the end sections 16, 18. A degree of curvature may be selected to minimize the presence of sharp corners on the segment and also to accommodate mounting of attachments thereon. For example, in some embodiments, curved sections 15, 17 may possess a curvature so that blade blocks 36 may be connected thereto. For example, in some embodiments, a user may slide a blade block 36 from intermediate section 20 to a curved section 15, 17 without disengaging the blade block 36 from the frame segment 12.

In some embodiments, the end sections 16, 18 may be defined by a length of a relatively straight section at the ends of the first frame segment 12. In other words, the end sections 16, 18 may comprise a portion of the frame starting where the curvature becomes negligible and extending to terminal points of the first frame segment 12.

In some embodiments, the length of the end sections 16, 18 may be minimized so as to reduce the overall width of the first frame segment 12 as a whole. This may be advantageous because the first frame segment 12 may sometimes be placed on top of the second segment 14 when the frame is assembled. And, in some cases, this operation may be executed underneath the arms of a surgeon or otherwise in a situation where space is limited. For example, in some embodiments, the end sections 16, 18 may include a mounting end surface, region, or tab upon which the connectors 28, 30 may be coupled. Accordingly, the connectors 28, 30 may be coupled to a frame segment 12 directly adjacent the curved sections 15, 17. For example, the end sections 16, 18 may simply comprise a terminal tab upon which the connectors 28, 30 may be coupled.

Figure 31:
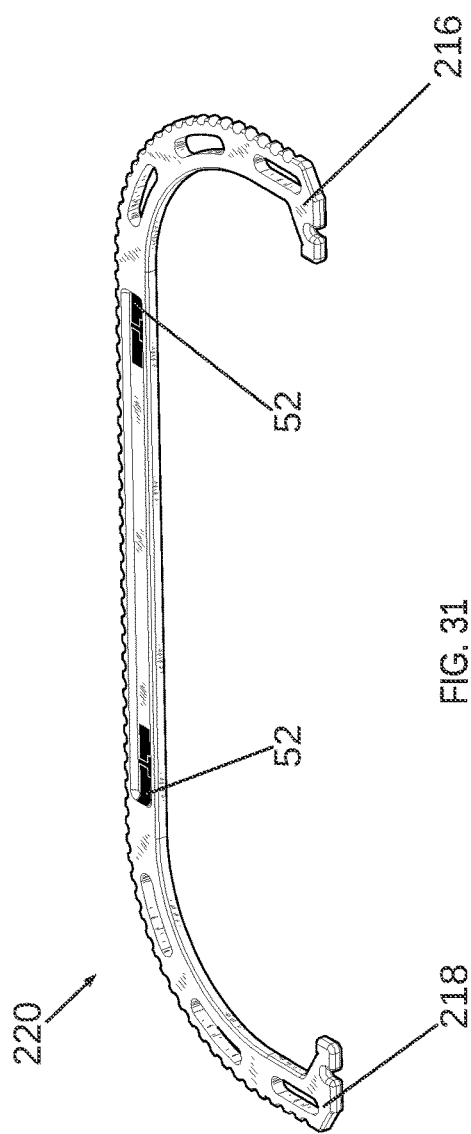
FIG. 31 shows an alternative embodiment of a frame segment of a surgical retractor.
Figure 32:
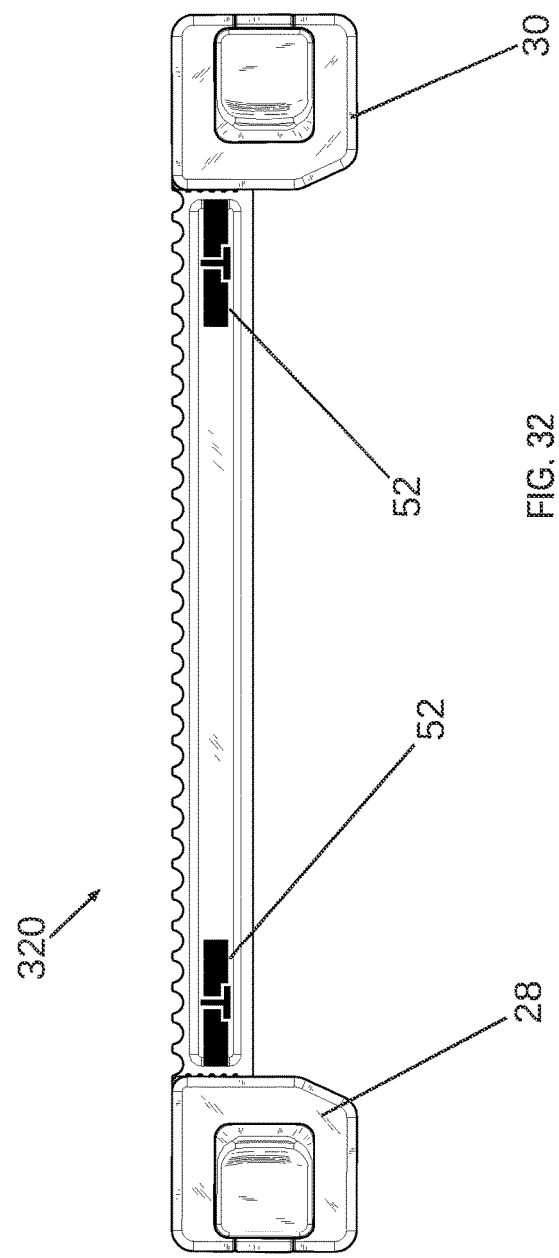
FIG. 32 shows another alternative embodiment of a frame segment of a surgical retractor.

For example, FIG. 31 shows an alternative embodiment of a first segment 220. As shown therein, connectors 28, 30 may be coupled (e.g., fixedly, or manually and reversibly mounted) to the first segment 220 using a terminal tab so that the connectors 28, 30 may be mounted directly adjacent to curved sections of the segment 220. In some embodiments, connectors 28, 30 may be modified for attachment directly to an intermediate section 20 without any curved sections therebetween. For example, FIG. 32 shows an alternative embodiment of a segment 320 with connectors 28, 30 mounted directly to the ends of an intermediate section 20.

In some embodiments, a first frame segment 12, 220, 320 may have a length of about 20, 25, 30, 35, 40, 45, 50, 60, 65, 70, 75, or 80 centimeters in length, including all values and ranges there between. In some embodiments, the length of a first frame segment 12, 220, 320 may be made so that at least two blade blocks 36 may be coupled to the first frame segment 12, 220, 320. The blade blocks 36 may further be spaced apart by a distance. For example, as shown in FIG. 1, a pair of blade blocks 36 are shown coupled to the first frame segment 12 and spaced apart along a length of the intermediate section 20. The blade blocks 36 may, for example, be positioned on a frame segment 12, 220, 320, such as at about the position of the visual indicators 52, so that the blade blocks 36 are spaced apart a recommended distance. With further reference to FIG. 1, another pair of blade blocks 36 may be coupled on the second frame segment 14. That additional pair of blade blocks 36 may also be spaced apart at a recommended distance. In this way, a frame may include two pairs of blade blocks with blade blocks 36 positioned near the corners of the frame. The blade blocks 36 on each of the frame segments 12, 14 may work together to help prevent unintentional movement and migration of the retractor blades along the edges of the surgical wound.

In some embodiments, the frame segment 12, 220, 320 may have a width of about 5, 7, 10, 15, 20, or 25 cm, including all values and ranges there between. For example, in the frame segment 320 the minimum width of the segment may only be limited by the width of the connectors 28, 30. This width may, for example, be minimized to solve the problem of how to engage a first frame segment 12, 220, 320 with a second frame segment 14 when a surgeon is already using the second frame segment 14 to pull back the tissue of a wound and engaged in a surgical procedure.

Figure 8B:
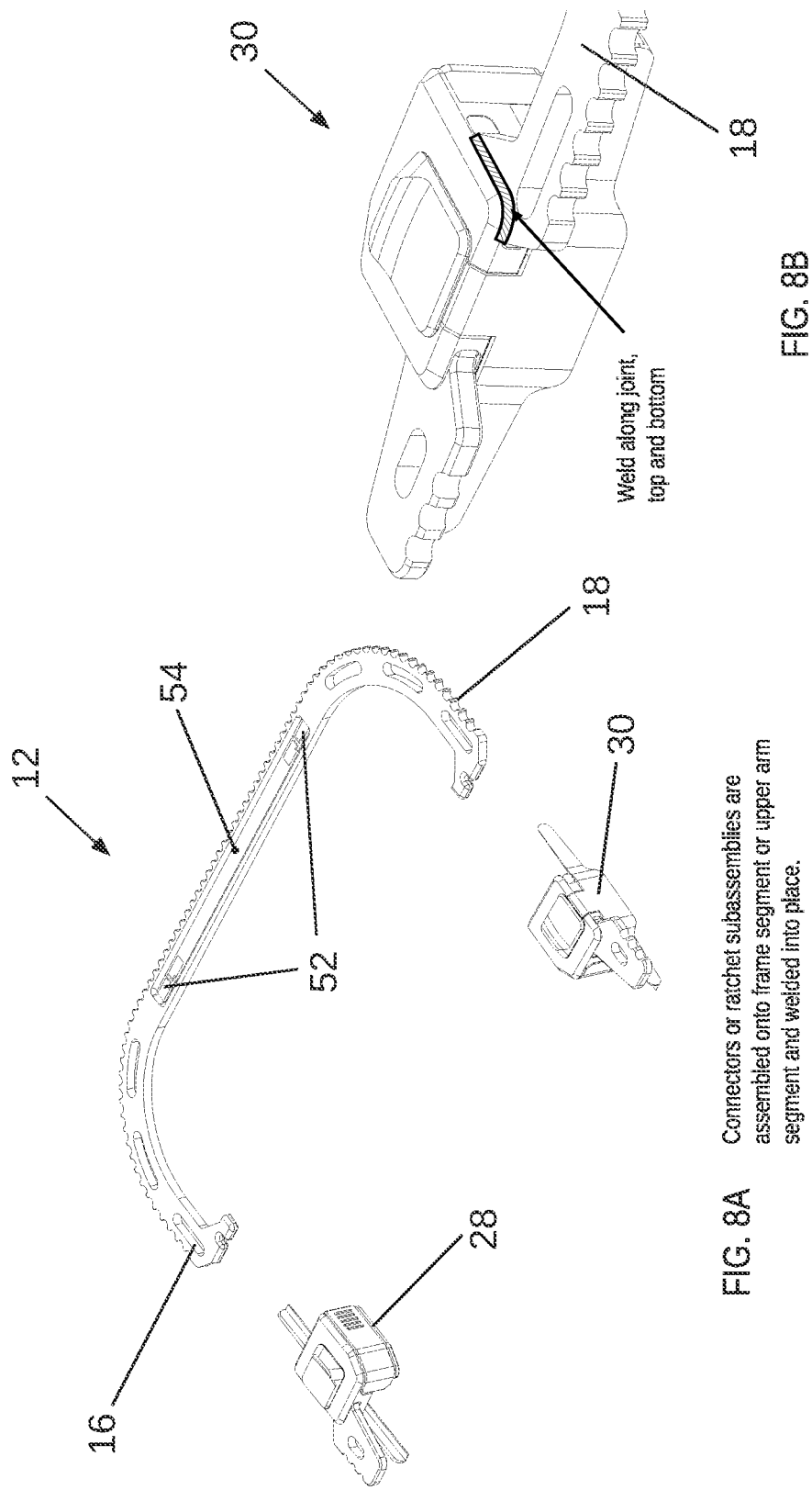
FIG. 8B shows an end of the frame segment shown in FIG. 8A and showing a rigid connection between the segment and a connector or ratcheting subassembly.

In some embodiments, frame segment 12 includes a pair of connectors 28, 30 which may be fixedly connected to respective end sections 16, 18. For example, as shown in FIG. 8A, the connectors 28, 30 (which may, in some embodiments, be ratcheting connectors and referred to as ratchet subassemblies) may be assembled on the frame segment 12 (which may sometimes be referred to as an upper arm segment), and the connectors 28, 30 may be welded (shown in FIG. 8B) along one or more joints so that the connectors 28, 30 are securely attached to a respective end section 16, 18. In such embodiments, the connectors 28, 30 may be considered as part of the frame segment 12. Alternatively, the connectors 28, 30 may be fixedly attached to the frame segment 12 in other ways such as using epoxy, glue, or some other suitable way so as to provide a rigid and secure connection therebetween. Thus, in some embodiments, the connectors 28, 30 may be fixedly or rigidly connected to the ends of frame segment 12, and the connectors 28, 30 may be configured for manually reversible connection to the second frame segment 14. Fixing the connectors 28, 30 to one segment has been found to be particularly advantageous in helping to prevent misalignment of the frame segments when expanding or collapsing the frame. This situation, which may be a common problem with other ratchet systems, may sometimes be referred to as "racking" and may cause a ratcheting assembly to cease up or jam making it difficult to adjust the frame. In other embodiments, the connectors 28, 30 may be configured for reversible attachment from both the frame segments 12, 14, i.e., the connectors may be manually attached and detached from both the frame segments 12, 14. Some of those embodiments may include one or more other features to help reduce a risk of racking.

Figure 9:
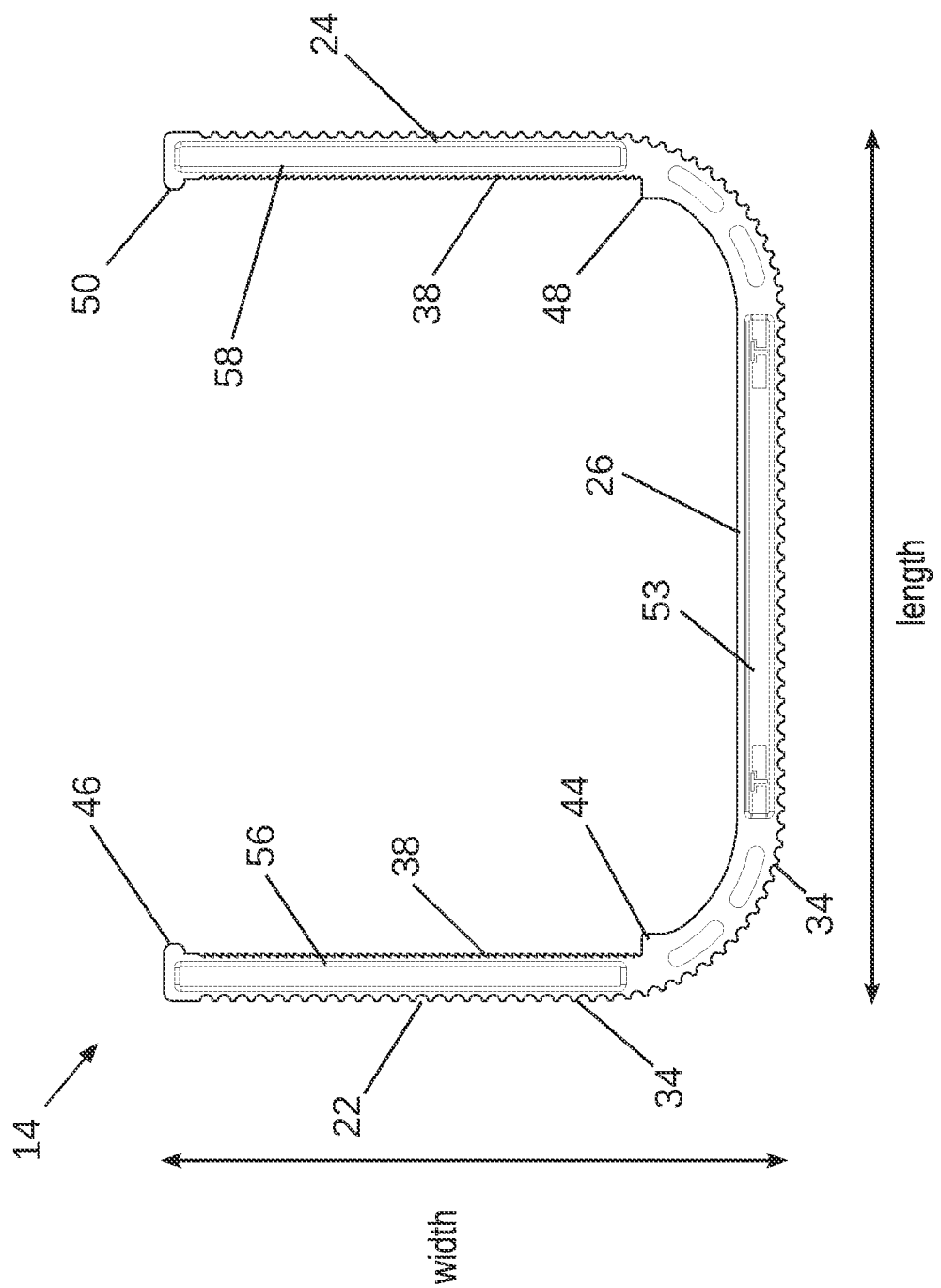
FIG. 9 shows a top plan view of an embodiment of a frame segment of a surgical retractor.
Figure 10:
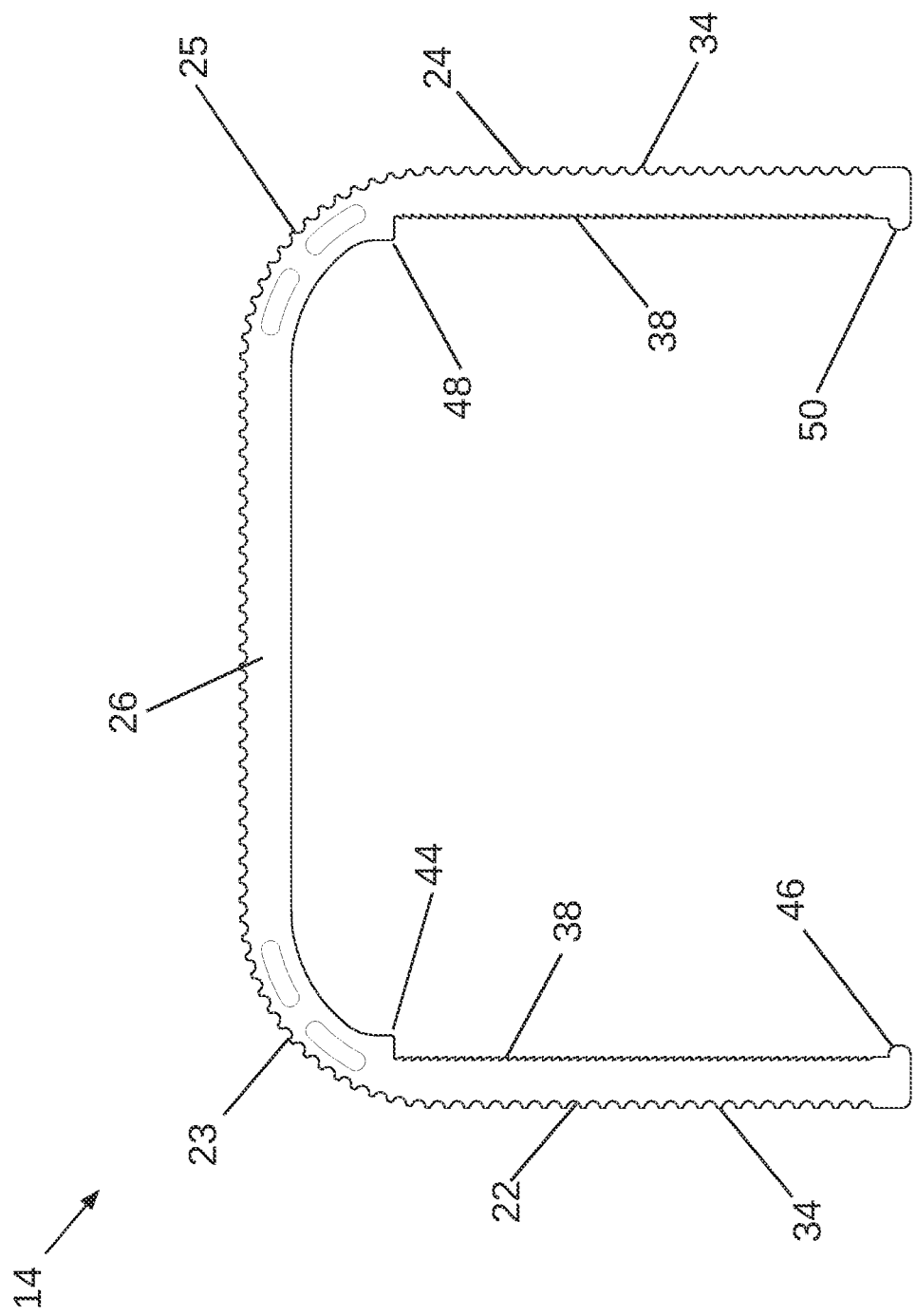
FIG. 10 shows a bottom plan view of the frame segment shown in FIG. 9.
Figure 11:
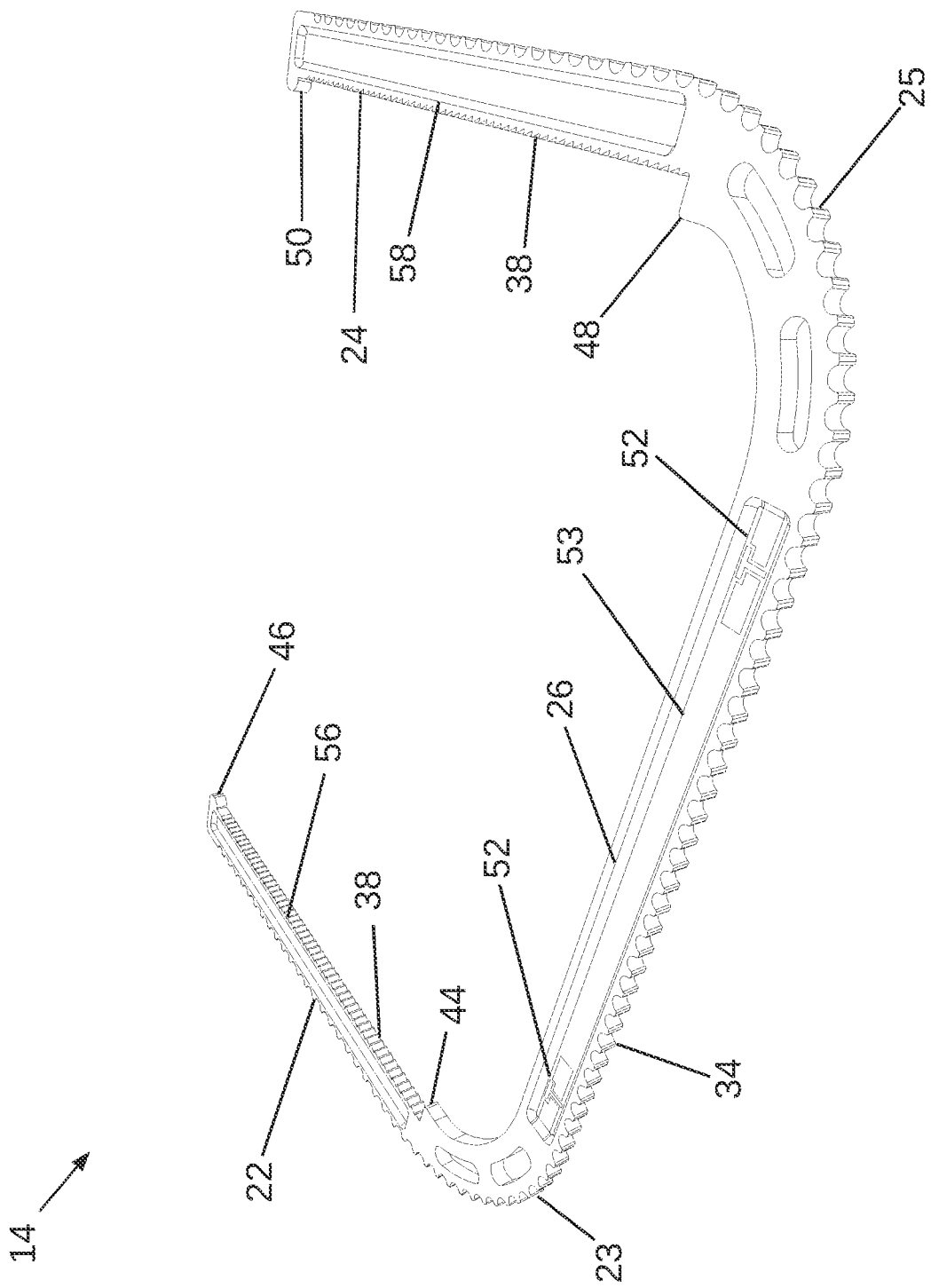
FIG. 11 shows a perspective view of the frame segment shown in FIG. 9.

Various embodiments of second frame segment 14 are further described in relation to FIGS. 9-11. For example, as similarly described for the first frame segment 12, the second frame segment 14 may include one or more visual indicators 52 indicating a position for suggested placement of blade blocks 36. Like the segment 12, the segment 14 may also allow for adjustable positioning and movement of blade blocks 36 thereon. For example, the segment 14 may include a central groove 53 and side grooves 56, 58. The grooves 53, 56, 58 may facilitate sliding adjustment of blade blocks 36 or other attachments connected to the segment 14. As an alternative to a plurality of grooves 53, 56, 58, a segment 14 may include a single groove (not shown), such as may extend across each of the end sections 22, 24, intermediate section 26 and curved portions 23, 25. Accordingly, in some embodiments, retractor blades 36 may slidably move within that single groove around substantially the entire length of the second frame segment 14. As most clearly shown in FIG. 11, each of the end sections 22, 24 may have teeth 38 along one or more edges, and/or ridges or grooves along one or more faces. For example, teeth 38 may be formed on an inner surface of each of the end sections 22, 24. The retractor 10 may be adjusted in size by moving the frame segments 12, 14 in relation to each other by moving the connectors 28, 30 along the teeth 38. In other embodiments, as opposed to moving on teeth 38, the connectors 28, 30 may move across grooves, ridges, or another suitable structure so as to allow for adjustable sizing of the frame.

In some embodiments, the frame segment 14 may include a length of about 20, 25, 30, 35, 40, 45, 50, 60, 65, 70, 75, or 80 centimeters in length, including all values and ranges there between. In some embodiments, the frame segment includes a width of about 15, 20, 25, 30, 35, 40, 45, or 50 cm, including all values and ranges there between. Notably, in this design the frame segment 12 may have a width that is significantly different from the width of the second frame segment. For example, where an assembled frame is expanded to a considerable overall width, such as a width of about 60 cm, about 50 cm, about 40 cm, about 30 cm, about 25 cm, or other suitable width, at least a majority of this width may be provided by the second frame segment 14. This geometry may be particularly advantageous in some embodiments wherein the second frame segment 14 is mounted on a wound or incision site before the first frame segment 12, because the smaller width frame segment 12 may be readily threaded underneath the arms of a surgeon during retractor assembly. For example, in some embodiments, the frame segment 12 width may be no more than about 75%, about 60%, about 50%, about 40%, or about 30% of the width of the second frame segment 14.

In some embodiments, various components of a surgical retractor, including associated blades and attachments, for example, may be provided in the form of a surgical retractor kit. FIG. 12 shows an embodiment of components that may be part of a surgical retractor assembly. The components may, for example, be provided to a consumer as a kit including first segment 12, second segment 14, blade blocks 36, and retractor blade assembly 60. Connectors 28, 30 may be provided in a form integrally connected to the first segment 12 or as separate components configured for reversible coupling thereto. Any number of attachments such as connectors 28, 30 and blade blocks 36 may be provided. For example, a kit may comprise a group of four separate blade blocks 36, although another number of blade blocks 36 may also be provided.

Various embodiments of connectors 28, 30 are further described in relation to FIGS. 13A-13C. In some embodiments, the connectors 28, 30 may be configured to operate using a ratcheting mechanism. Accordingly, the connectors 28, 30 may sometimes be alternatively referred to as left and right ratcheting subassemblies. The two subassemblies may comprise left and right versions which may be substantially the same except that the two subassemblies may comprise chiral ratchet housings. In this context, the designation of "left" and "right" denotes a reference frame with a patient lying face up and oriented so as to expose the patient's abdominal cavity and wherein each of the first segment 12 and second segment 14 may be oriented to lie laterally across the patient. In this exemplary situation, the first segment 12 may sometimes be located in a superior orientation "closer to the patient's head" with respect to the second segment 14. Therefore, the connector 28 may be positioned on the right-side of the patient's body and the connector 30 may be positioned on the left-side of the patient's body. Likewise, when used in this exemplary way, the first frame segment 12 may be referred to as the upper segment or upper arm and the second frame segment 14 may be referred to as the lower segment or lower arm. However, the retractor 10 may be positioned differently depending, for example, on the orientation of an incision or wound in the abdominal cavity and or preference of the surgeon. For example, as opposed to lying laterally from right to left on the patient's body the first segment may lie along a longitudinal axis along the direction from head to toe of the patient. Accordingly, the frame segments 12, 14 may sometimes be referred to as upper arm or lower arm segment. However, this terminology should not be taken as limiting the segments as only suitable for use in one particular orientation.

Using this reference frame, components of the "left" side connector 30 are shown in FIG. 13B. As shown therein, the connector 30 may include ratchet actuator 62, spring 64, ratchet or connector housing 66, dowel pin 68, first compression spring 70, slide lock 72, second compression spring 74, ratchet fastener 76, and dowel pin 78. Spring 64 may, for example, be a torsion spring, a leaf spring, or some other suitable spring or element may be used. Ratchet fastener 76 may, for example, comprise a clamp, brace, or clasp. The "right" side ratchet may include similar components. FIG. 13C shows perspective views of the "left" side connector 30 oriented so as to show both the top side and the bottom side of the connector 30. As shown from the top side perspective view, the connector 30 may include a wing 42 upon which a standard attachment, such as a Bookwalter attachment, may be attached. As shown in the bottom side perspective view, the connector 30 may include a channel 82 including a feature 80, such as a ridge, suitable for coupling with the groove 58 (shown on end section 24 of frame segment 14) so that the connector 30 may slide along frame segment 14 when the frame is assembled and when the ratchet is disengaged. Of course, the "right" side connector 28 may have similar components except that the ratchet housing 66 may be shaped as a mirror image. In some embodiments, the feature 80 and groove 58 may only allow the connector to properly couple with an appropriate end section or surface of a frame segment. To further help guarantee that an appropriate end section and connector are couple and/or coupled in a proper orientation one or more surface markings may be included on one or more of the connectors 28, 30 and frame segments 12, 14. For example, in some embodiments, each of the connectors 28, 30 and end sections 22, 24 are marked or color coded to help guide a user in properly assembling the retractor frame. Although the above features are explained with feature 80 as a ridge and a complementary groove 58, it should be understood that other complementary structures may be used. For example, feature 80 could be a groove and a ridge could replace the groove 58 on the end sections 22, 24. The mechanism for using the connectors 28, 30 so as to couple the first frame segment 12 to the second frame segment 14 is further explained with respect to FIGS. 14-16, for example.

With reference to FIGS. 14-16, the connectors 28, 30 may be used to couple segments 12, 14 together during frame assembly. The connectors 28, 30 may sometimes also be used to disengage the segments 12, 14 such as may be used to dismount a retractor from a wound or incision site. Notably, this may be done even in situations where collapsing the frame before frame removal is not a viable option. During retractor assembly, if necessary (e.g., if the connectors are not already fixedly or otherwise attached to the first frame segment 12), a user may attach the connectors 28, 30 to the first frame segment 12. A user may then connect segment 12 to the segment 14 by aligning each connector 28, 30 so that a channel 82 of the respective connector is overlaid with an appropriate end section 22, 24 of frame segment 14. For example, right-side connector 28 may be aligned so that the end section 22 of the frame segment 14 is about parallel with the long axis of the channel 82 and the structures may be overlaid. For example, the structures may be overlaid when the connector 28 is lowered on top of the end section 22. Of course, a user may alternatively overlay the connector 28 and frame segment 14 by raising the frame segment 14 so that that the end section 22 becomes seated within the channel 82, or both structures may be moved together. Likewise, left-side connector 30 may be aligned so that the end section 24 of the frame segment 14 is about parallel with the long axis of the channel 82 on the connector 30 and the structures may be overlaid. Importantly, the engagement of the two frame segments 12, 14 may be accomplished by changing the relative vertical positions of the frame segments 12, 14 and does not demand that the two frame segments are brought together in an end-to-end style for engagement (i.e., with the terminal ends of each frame segment aligned in the same vertical plane) so that the ends of each frame segment may be passed through one or more holes or lumens in a connector.

With the connectors 28, 30 aligned with respect to the end sections 22, 24 a user may slidably unlock the slide lock 72 so as to unlock the ratchet fastener 76. For example, the ratchet fastener 76 may rotate as shown in FIG. 14 (e.g., via sliding movement of slide lock 72 and spring actuation) so as to open the channel 82 so that end section 22 and the connector 28 may be brought together with end section 22 being seated within the channel 82, i.e., the ratchet fastener 76 may be rotated to allow the lower arm "frame segment 14" to nest into the connector 28. Likewise, the connector 30 may be brought together with end section 24 being seated within channel 82 of the left side connector 30 (shown in FIG. 16). Once the end sections 22, 24 of the lower arm or frame segment 14 are seated within respective channels 82 of the connectors 28, 30 a user may release the slide lock so that the ratchet fastener 76 rotates so as to lock the segments 12, 14 together. In some embodiments, ratchet fastener 76 may include a lip 90 or other suitable feature so as to help lock the end sections 22, 24 within the channel 82 and help hold the frame segments 12, 14 together.

The connector 28 may be coupled to the end section 22. For example, the connector 28 may be coupled to the end section 22 near the distal end of the end section 22 adjacent the expansion stop 46. However, the connector 28 may also be coupled to the end section 22 at a proximal end of the section 22 adjacent the contraction stop 44. Thus, advantageously, the segments 12, 14 may be coupled together in either of a fully expanded configuration, fully collapsed configuration, or at some intermediate state. This may make retractor assembly easier, particularly in situations where a surgeon may already be engaged with the patient and where the frame segment 12 must be inserted underneath the arms of a surgeon and then coupled to the frame segment 14. For example, a surgical team member may quickly adjust the position at which the frame segments 12, 14 are coupled together based on the position of the surgeon's arms as opposed to making the surgeon move so that the frame segments 12, 14 may be coupled together in a required way.

Figure 17:
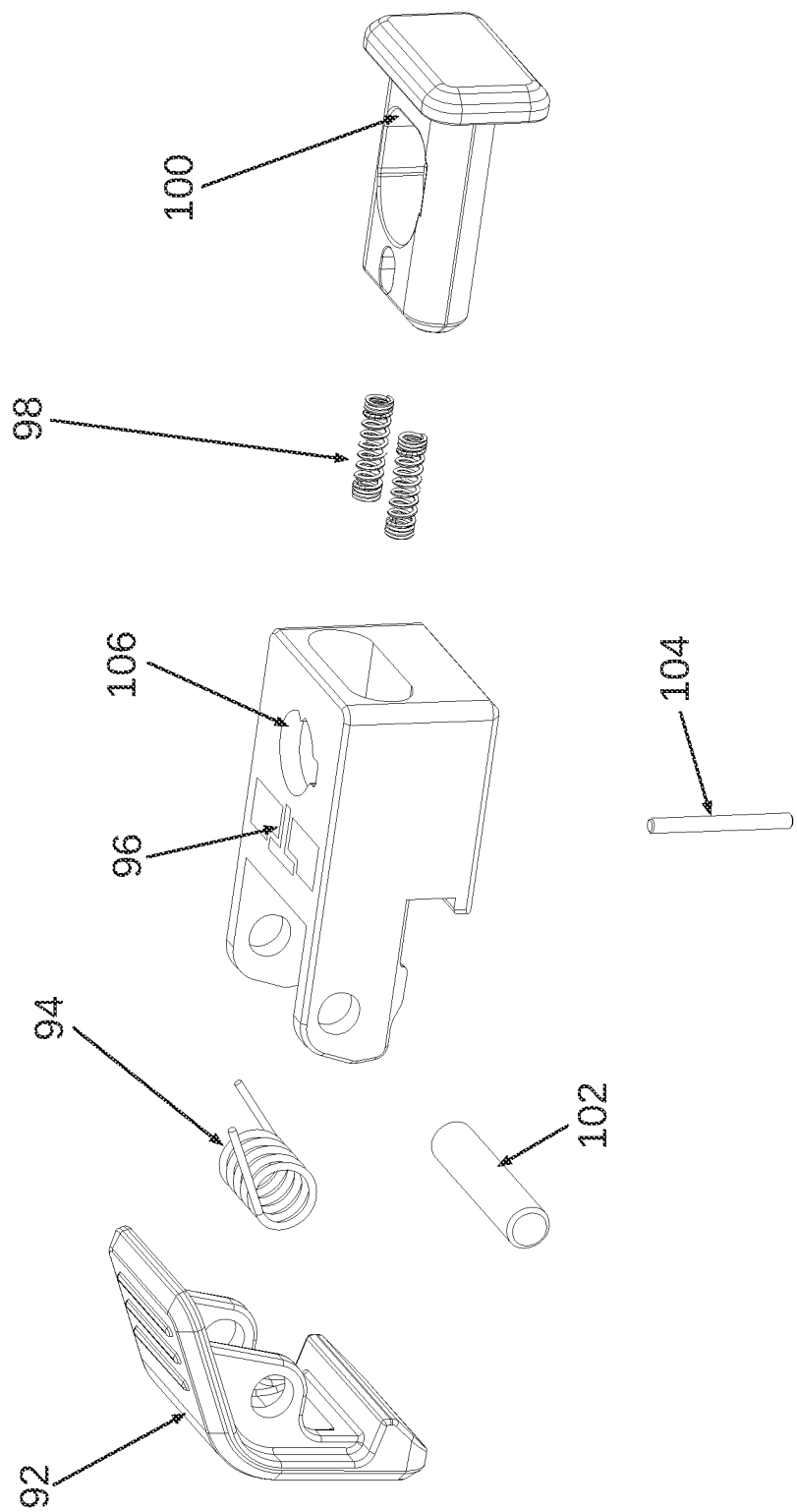
FIG. 17 shows an embodiment of components used to construct a blade block.
Figure 19:
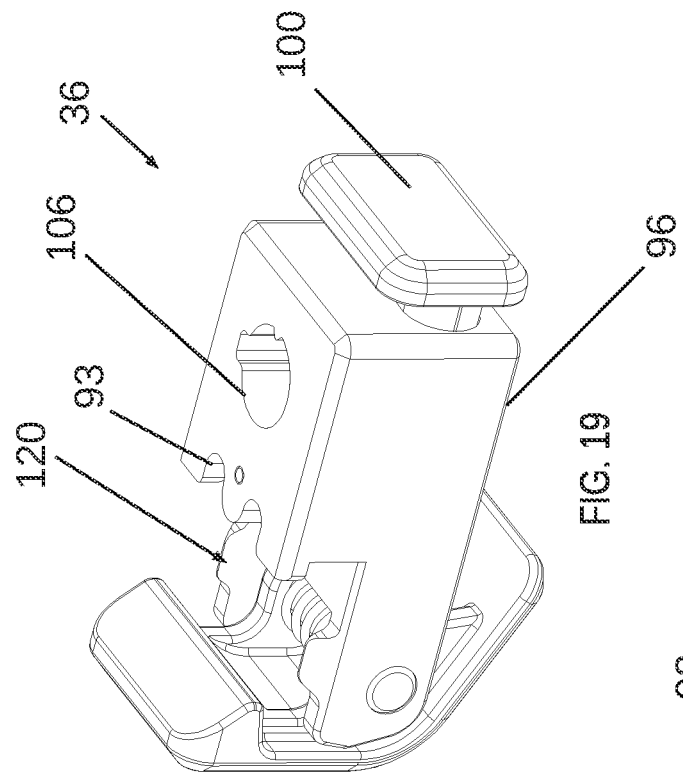
FIG. 19 shows a perspective view of a blade block oriented so as to show a bottom-side surface thereof.
Figure 18:
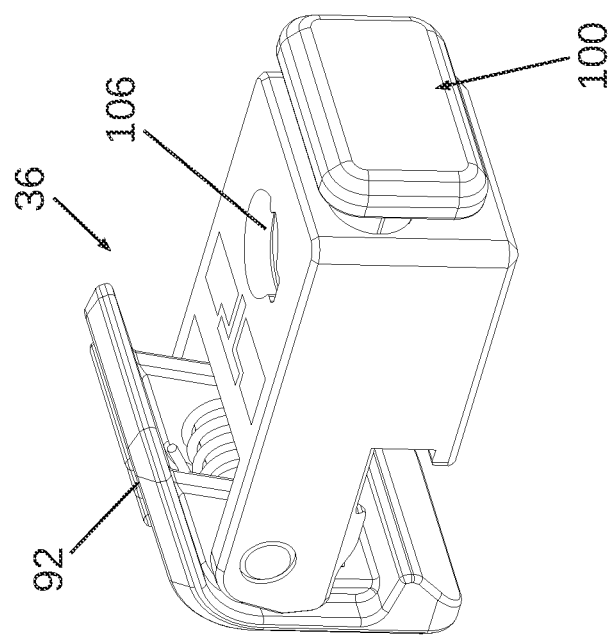
FIG. 18 shows a perspective view of a blade block oriented so as to show a top-side surface thereof.
Figure 20:
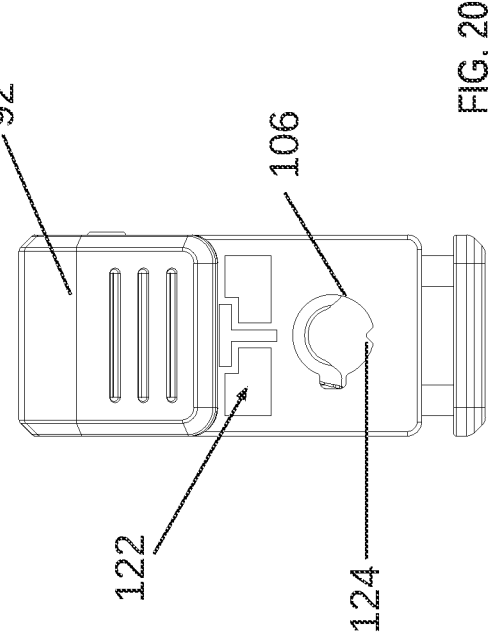
FIG. 20 shows a top plan view of the blade block shown in FIGS. 18 and 19.

FIGS. 17-20 show an embodiment of the blade block 36 and associated components in various orientations. As shown in FIG. 17, blade block 36 may include a number of components including by way of nonlimiting example a pivot button 92, torsion spring 94, blade block housing 96, one or more compression springs 98, push button 100, and dowel pins 102, 104. As an alternative to torsion spring 94, a leaf spring or other suitable element may be used. FIG. 18 and FIG. 19 show perspective views of the blade block 36 in orientations so as to show the top side of the blade block in FIG. 18 and the bottom side of the blade block 36. During retractor assembly or use, a user may press on the pivot button 92 so as to release the blade block 36 from a locked position so as to allow for adjustment of the blade block 36 along the perimeter of the frame. For example, when the pivot button 92 is pressed, a biasing force urging the teeth 32 or 34 of either frame segments 12 or frame segment 14 against corresponding grooves 93 (which may be formed in the blade block housing 96 as best shown in FIG. 19) may be withdrawn so that the blade block 36 may be moved along the frame. In some embodiments, the blade block may include a ridge or other feature 120 suitably shaped so that the blade block 36 may only be mounted on the frame in a correct orientation, i.e., with the ridge 120 seated within one or more of groove 54 of frame segment 12 or the grooves or 53, 56, 58 of frame segment 14. As shown in FIG. 20, a blade block 36 may include a visual indicator 122 to aid in proper placement of the blade along either of the frame segments 12, 14. One or more features 124, such as a knob or ridge may be configured to prevent free rotation of the blade post within the housing 96, as explained in greater detail in FIG. 25.

As further shown in the FIGS. 17-20 blade block 36 may include an opening 106 suitable for receiving a blade post 110 (the blade post 110 shown in FIGS. 21-23, for example). For example, the push button 100 may allow a user to raise and lower a retractor blade. With further reference to FIG. 24A and FIG. 24B, blade assembly 60 may be mounted to a blade block 36 by inserting blade post 110 within the opening 106. Push button 100 may be actuated to allow the blade post 110 to slide through the opening 106. Once the blade 114 is at a desired height, a user may release the push button 100 to lock the blade 114 in place. In some embodiments, the blade post 110 may include one or more grooves 130. In order to seat within the blade block housing 96, the blade post 110 may be vertically adjusted so that at least one of the grooves 130 is properly engaged within the opening 106. For example, in some embodiments, when a selected groove 130 is positioned within the opening 106, a user may be provided an audible click or receive a tactile indication that a selected groove 130 has become seated. Alternatively, the grooves 130 may provide a visual indication of the vertical position of the blades 114. Thus, in some embodiments, a specific vertical height of a blade 114 may be selected based on which of the one or more ridges 130 is selected. Because a specific vertical height of a blade 114 may be selected, blades on different positions on the frame may be set to the same vertical height or to different heights. Accordingly, tension on walls of a wound or incision may be more accurately controlled than in other retractors. For example, blades on opposite sides of a frame may be set to a vertical height so that the blades are at the same level. In some embodiments, grooves or other markings may be established so as to allow a user to readily level blades on opposite sides of a frame even if the frame segment to which the blades are attached are at different heights. For example, the grooves may be set in gradation units that match the height difference between opposite sides of the frame.

Various embodiments of the retractor blade assembly 60 are further described in relation to FIGS. 21-23. As shown in FIG. 21, retractor blade assembly 60 may include a blade 114, blade post 110, and dowel pin 112. In some embodiments, the dowel pin 112 may act as a directional feature to prevent incorrect insertion of the blade assembly 60 into a blade block 36. In some embodiments, blade 114 may be welded to the blade post 110 or the blade 114 and blade post 110 may be coupled in some other way. In some embodiments, a retractor blade assembly 60 may be configured so that the assembly 60 may rotate over a controlled angle when mounted in a blade block 36. For example, as shown in FIG. 23, the blade post 110 may include a flat portion shaped so as to create a surface that limits blade rotation, such as to an angle of about 90 degrees (45 degrees in each direction from the centerline as shown in FIG. 25), or blade rotation may be limited to some other suitable angle. A blade 114 may, for example, be limited in rotation so that it may be automatically oriented at least generally in a proper orientation during retractor assembly, thereby facilitating rapid assembly of the retractor 10. For example, as shown in FIG. 26A and FIG. 26B the retractor blades 114 may be rotationally limited about an angle of about 90 degrees or some other suitable angle. In some embodiments, a retractor blade 114 may be rotationally limited over a range of about 120 degrees to about 60 degrees.

FIGS. 27A-C shows an embodiment of a mechanism in which a blade block 36 may be mounted to a frame segment. For example, as shown in FIG. 27A, a blade block 36 may be positioned on the frame, such as near a recommended attachment point as may be indicated via one or more of the visual indicators 52 included on a given frame segment 12, 14. The visual indicators 52, 122 (not visible from the side view shown in FIG. 27A) may provide an indication as to how to orient the blade block 36 for mounting. For example, when the blade block 36 is oriented so that a "T" on the visual indicator 122 is aligned so as to overlay with a corresponding "T" on the visual indicator 52 of the frame, the user may know that the blade block is properly oriented for mounting. As shown in FIG. 27B, the blade block 36 may be angled onto a frame segment 12, 14 upon which the blade block is being attached, so that the frame segment 12, 14 is inserted within an inner ledge of the blade block 36. The blade block 36 may then be rotated into place. Without actuating the pivot button 92 (e.g., when releasing the pivot button 92), the blade block 36 will snap into place on the frame. As shown in FIG. 27C, when properly assembled, the ridge 120 on the blade block 36 may be nested into the groove or slot on the frame segment on which the blade block 36 was attached. For example, in FIGS. 27A-C, the groove 54 is shown. When properly assembled, a lip 122 may help to hold the blade block 36 on the frame. Notably, if the blade block 36 were incorrectly assembled backwards, upside-down, or in an incorrect position, the blade block 36 may not lock in place as the lip 122 would not properly engage the frame.

In some embodiments, a blade block 36 may be positioned around the frame. FIGS. 28A-C show an embodiment for how a blade block 36 may be adjustably positioned on a frame or frame segment 12, 14. FIG. 28A shows blade block 36 in one possible initial position as mounted on the retractor frame or on an individual frame segment. For example, as shown in FIG. 28A, the blade block 36 is shown mounted to the frame segment 14. As shown in FIG. 28B, pivot button 92 may be actuated and the blade block 36 may be moved in a direction so as to disengage the teeth 34 from a corresponding groove 93 (shown more clearly in FIG. 19). This may provide for clearance of the blade block 36 to be slid along the frame to a desired position. Notably, in this action, the blade block 36 does not have to be removed from the frame. As shown in FIG. 28C once the blade block 36 is moved to a desired position, pitot button 92 may be released so as to force the teeth 34 to reengage with the grooves 93 so as to lock the blade block 36 in place.

Figure 29B:
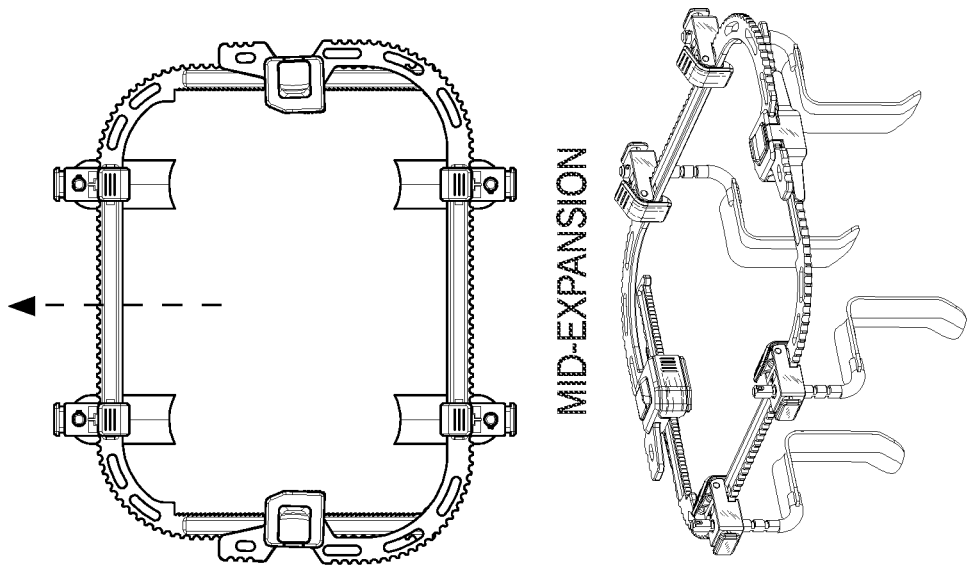
FIG. 29B shows each of a top plan and a perspective view of an assembled frame in a mid-expanded configuration.
Figure 29A:
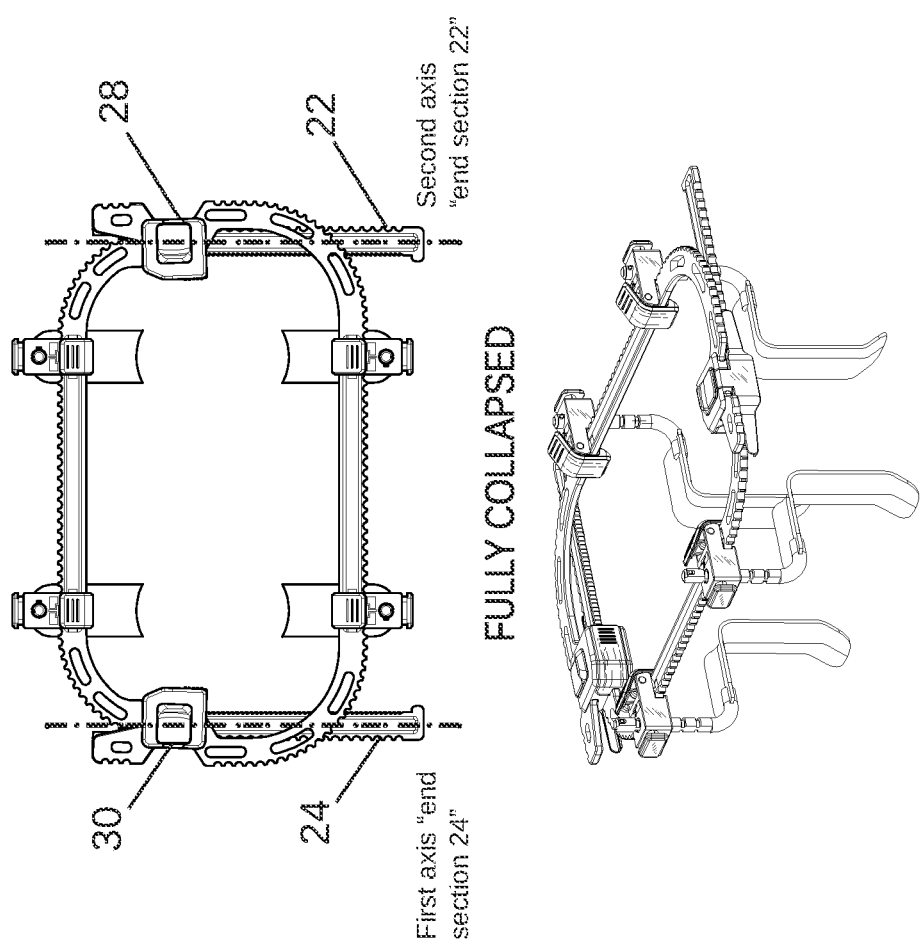
FIG. 29A shows each of a top plan and a perspective view of an assembled frame in a fully-collapsed configuration.

Advantageously, the surgical retractor 10 may be first positioned over an incision in any of a fully collapsed, intermediate expanded, or fully expanded state. The frame may then be expanded and collapsed as may be needed during a surgical procedure. For example, as shown in FIGS. 29A-C, retractor 10 may be assembled in a position that is about fully collapsed as shown in FIG. 29A. To adjust the frame, a user may, for example, hold the upper and lower arms (i.e., the first segment 12 and second frame segment 14) and expand the frame outwards. In this approach, the connectors 28, 30 may be disposed along the end sections 16, 18 of the first frame segment 12 and are further coupled to respective end sections 22, 24 of the second frame segment 14. When expanding the frame, the connectors 28, 30 may slide along the length of the end sections 22, 24 which lie along the first and second axes which are substantially parallel. In this design, the connectors 28, 30 move together along the end sections 22, 24 and maintain relative alignment between each other. The retractor 10 may include any number of design features to help prevent any type of misalignment that might cause the frame racking (e.g., where the frame may unexpectedly lock in place).

In some embodiments, risk of racking is minimized by the manner of coupling between the connectors 28, 30 and the end sections 22, 24. For example, the connector 28 may include a ridge or other feature 80 that moves along the groove 56. Likewise, the connector 30 may include a ridge or other feature 80 that moves along the groove 58. More generally, the connectors 28, 30 may include a channel 82 including one or more feature that is complementary in shape to a corresponding feature on the end sections 22, 24 so as to help constrain the end sections 22, 24 in the channel 82 and prevent the end sections 22, 24 from twisting in response to any jarring motion on the frame which might otherwise inadvertently misalign the frame segments 12, 14. That is, the end sections 22, 24 may be held firmly in the channel constrained therein and held within a complementary shaped groove or ridge in the channel. The channel 82 itself may be sized so as to help prevent racking. For example, in some embodiments, the channel 82 may be at least about 2, 4, 6, 8, or about 10 cm in length so as to provide a significant area for contact between the connector and the end sections 22, 24. The extended contact surface within the channel helps to maintain the end sections 22, 24 and the connectors 28, 30 in a required alignment to minimize risk of racking.

In some embodiments, risk of racking may be minimized by fixedly connecting the connectors 28, 30 to the frame segment 12. Accordingly, relative motion between a connector 28, 30 and the end 16, 18 on which it is attached may be significantly reduced and substantially eliminated. In some of those embodiments, the connectors 28, 30 themselves may be fixedly connected because the frame segment 12 is itself rigid and each connector 28, 30 may be welded or otherwise rigidly fixed thereto. This rigid design may help to minimize frame warping and/or any effect of bowing so as to help promote smooth sliding of the frame during adjustment and help to prevent misalignment of the frame that might cause racking.

In some embodiments, one or more of the end sections of either or both of the frame segments 12, 14 may be tilted or canted so that the end sections (16, 18 and/or 22, 24) are not perfectly parallel with each other. For example, in some embodiments, the end sections 16, 18 may be configured with a small outward cant so as to angle the connectors 28, 30 (attached to the end sections 16, 18) away from each other. This angle is not so great so as to significantly interfere with expansion or contraction of the frame. However, the outward cant of the end sections 16, 18 creates a force between the connectors 28, 30 and the end sections 22, 24 of the second frame segment 14 (when those end sections 22, 24 are received within channels 82 of the connectors 28, 30) so as to substantially reduce a risk of frame misalignment and racking. For example, when the end sections 22, 24 are seated within the connectors 28, 30, a biasing force may be provided between the end sections 22, 24 and the channels 82 so as to counteract the types of jarring forces on the frame which might otherwise inadvertently misalign the frame segments 12, 14. Alternatively, as explained below, an angle between the channel 82 and an end section 22, 24 received therein may provide a biasing force that tends to relieve stress caused by frame misalignment so as to help minimize the severity of racking. For example, this biasing force may tend to realign the frame segments when a user expands or contracts the frame.

For example, as shown in FIG. 34A, an outward cant to the end sections 16, 18 may be characterized by the angles $A_1$, $A_2$. The angle $A_1$ shows the angles between an axis parallel to the intermediate section 20 of the frame segment 12 and the connector 30. The angle $A_2$ shows the angles between an axis parallel to the intermediate section 20 of the frame segment 12 and the connector 28. Generally, even small positive angles $A_1$, $A_2$ may work to significantly reduce a risk of racking. For example, in some embodiments, the angles $A_1$, $A_2$ would be about the same and each range from about 90.05° to about 90.65°. In other embodiments, angles $A_1$, $A_2$ would each range from about 90.10° to about 90.60° or about 90.15° to about 90.55° or about 90.18° to about 90.38°. In the embodiment shown in FIG. 34A, the angles $A_1$, $A_2$ are show with respect to the connector as a whole so that the channel 82 (which is generally parallel with the connector housing) is positioned at the same angle with respect to the intermediate section as is the connector housing as a whole. However, in some embodiments, a connector may be configured so that the channel 82 formed therein is angled with respect to the connector housing. In this case, simply angling the channel 82 so that it includes an outward cant (even without angling the end section upon which it is mounted), would have a similar effect as would the embodiment shown in FIG. 34A. That is, another end section would be received within the outwardly canted channel 82 at an angle so that similar forces would be created between the channel 82 and the end section received therein to help relieve a stress formed by racking.

Figure 34C:
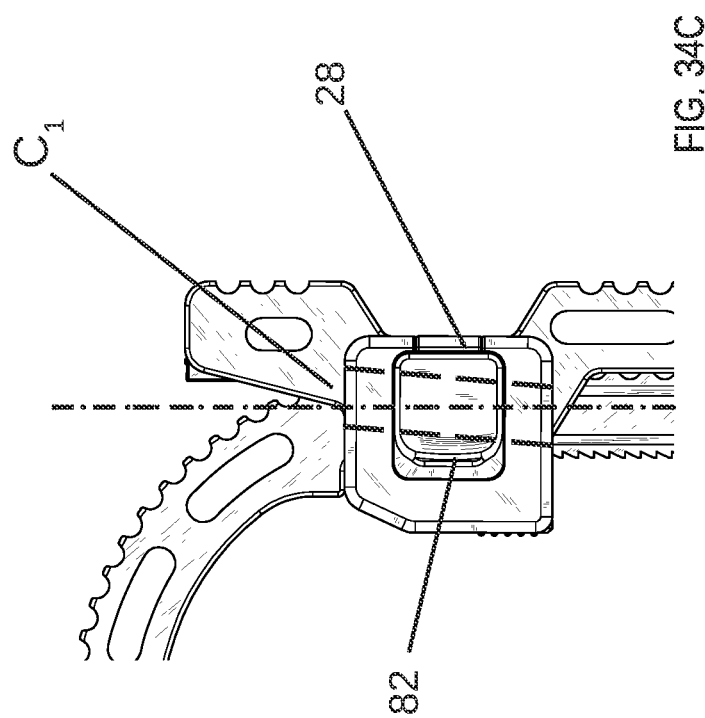

Similarly, as also shown in FIG. 34B, an angle B may be used to indicate the relative angle between the connectors 28, 30. In some embodiments, the angle B ranges from about 0.01° to about 1.30°. In some embodiments, the angle B may range from about 0.10° to about 0.76°. In some embodiments, the angle B may include a range of angles including a minimum angle of about 0.0°, 0.1°, 0.2°, 0.3°, and 0.4°. In some embodiments, the angle B may include a range of angles including a maximum angle of about 1.30°, 1.00°, or about 0.76°. Again, although the angle B is shown in FIG. 34B with respect to the connector as a whole, a similar effect could be achieved by making a connector with a channel angled with respect to a connector housing. For example, as shown in FIG. 34C, a channel 82 of a connector 28 may be tilted at an angle (shown by dot-dash lines) so that the channel is biased at an angle Ci within the connector housing. Likewise, in some embodiments, a connector 30 may be similarly tilted at an angle with respect to a connector housing. In some embodiments, a channel 82 may be tilted or angled with respect to an end section received therein based on any combination of angling the channel 82 with respect to a connector housing, canting of end sections to which a connector is mounted, angling of end sections received within the channel, or any combinations thereof.

Generally, any number of the above strategies for eliminating racking may be combined together. For example, in some embodiments, all of the above strategies may be combined together so as to substantially eliminate racking. Moreover, even in the rare case that the two frame segments 12, 14 do become slightly misaligned (such as may be the case when the frame is purposefully twisted and jarred), it has been found that any increased force that is needed to expand or contract the frames due to racking may be easily relieved. For example, in embodiments wherein the first frame segment 12 includes end sections 16, 18 configured with a small outward cant, applying an opposite force (e.g., releasing the ratchet and collapsing the frame) will relieve any increased force necessary to expand the frame.

In the embodiment shown in FIGS. 29A-C, the connectors 28, 30 do not need to be pressed during expansion. In other words, the frame may expand freely until a desired distance (or tension) is met. For example, as the frame is expanded the walls of a patient incision may begin to press against each of the two frame segments 12, 14. A user may release the frame and the system may remain in place due to tension of blades against the incision. The ratchet assembly of the connectors 28, 30 may hold the desired tension until deliberately released by the user.

As shown in FIGS. 30A-B, the surgical retractor 10 may be collapsed. For example, starting from a fully expanded position (shown in FIG. 29C) a user may simultaneously press both ratchet actuators to release the ratchet lock. With the ratchet lock released, a use may guide the system from a mid-expansion state (shown in FIG. 30A) into a collapsed state as shown in FIG. 30B.

Figure 33:
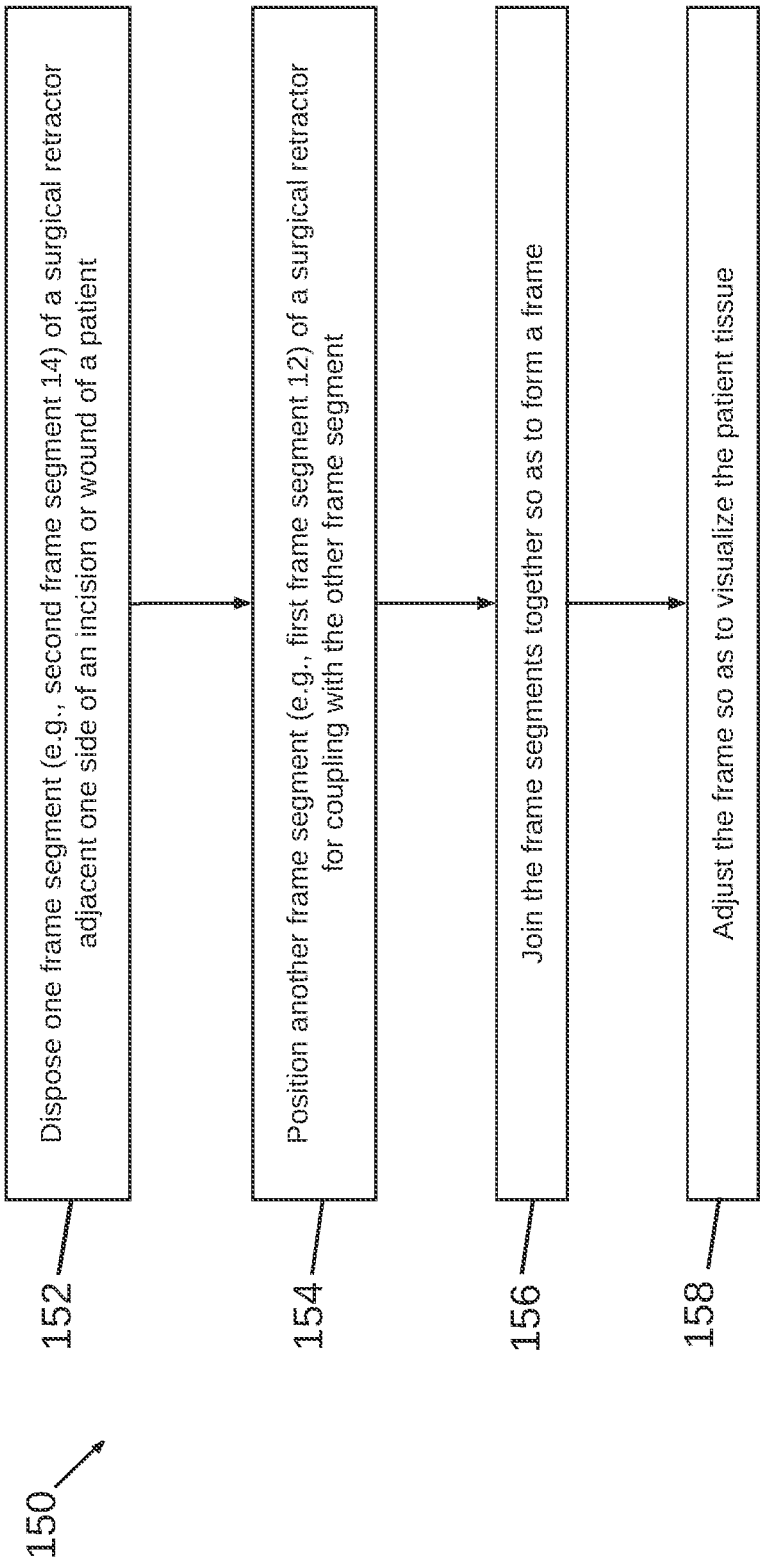
FIG. 33 shows an embodiment of a method for assembling a surgical retractor.

The surgical retractor 10 may be used in various ways for different surgical procedures. For example, FIG. 33 shows an embodiment of a method 150 for surgical retractor assembly and use. In step 152, one frame segment of a surgical retractor may be disposed adjacent one side of an incision or wound of a patient. For example, the frame segment 14 may sometimes be disposed on an opposite side of the surgical table from a side on which the surgeon or primary surgeon is standing. In some embodiments, together in step 152, the frame segment may be used to at least in part pull back a wall of the incision or wound so as to help visualize the patient's internal tissues. For example, the frame segment 14 may have at least one blade assembly 60 (e.g., a pair of blade assemblies) mounted therein. A blade assembly 60 may be held within a blade block 36 so that a front side face 115 of the blade 114 is at least generally disposed towards a wall of the wound or incision. The front side face 115 of the blade 114, may for example, be angled or shaped so as to facilitate proper contact to the wall of a wound or incision so that the blade 114 may properly pull back or otherwise hold the wall as intended. In some embodiments, the blade 114 may be allowed to rotate within the blade assembly 60 over a limited range of rotation so as to prevent the face 115 from turning so that it is not correctly oriented towards a wall of a wound or incision with which it is intended to engage.

In a step 154, the frame segment 12 may then be positioned with respect to the frame segment 14 so that it may be coupled thereto in order to form a frame. For example, the frame segment 12 may be positioned so that ends sections 16, 18 of the frame segment 12 are aligned about in parallel with the end sections 22, 24 of frame segment 14. In some situations, this may involve threading the frame segment 12 underneath one or more outstretched arms of a surgeon already performing a medical procedure. For example, as shown in FIG. 33B In a step 156, the frame segments 12, 14 may be joined together. For example, as also described in relation to FIG. 14, a user may slide the slide lock 72 so as to rotate the ratchet fastener 76 so that the frame segment 14 may be directed into a channel 82 within the ratchet housing 66. Once the frame segment 14 is seated therein a user may release the slide lock 72 so that the fastener 76 engages the frame segment 14. The segment 12 is designed so that a use may operate both connectors 28, 30 at about the same time so as to rapidly couple the two segments 12, 14 together. Notably, the frame segment 12 may be aligned with frame segment 14 and coupled thereto anywhere along the length of the end sections 22, 24. For example, in some situations, it may be advisable to couple the segments 12, 14 so that the frame is assembled in a collapsed state. This may, for example, make it easier to grasp one or more walls of the incision which may not be fully separated. However, alternatively, the segments 12, 14 may be coupled so as to form a frame in some mid expanded state or even a fully expanded state. This may, for example, be necessary if the surgeon has already begun to engage the patient in a medical procedure and where the first segment 12 and second segment 14 must be brought together so as to avoid knocking into the surgeon's arms.

As shown in step 158 the frame may be adjusted, as may or may not be necessary, so as to effectively visualize the patient's internal tissues. For example, as also described in relation to FIG. 29 to adjust the frame, a user may hold the upper and lower arms (i.e., the first segment 12 and second frame segment 14) and expand the frame outwards. Other attachments may likewise be attached as may be desired to complete retractor assembly.

As described in detail above, the present application is directed to surgical retractors and associated components, such as frame segments, blade blocks, and ratcheting connectors, that may be used in surgical procedures, such as abdominal surgeries. Persons of ordinary skill in the art will understand that the surgical retractors and associated components as described herein may be utilized with other suitable surgical procedure. Likewise, persons of ordinary skill in the art will understand that components herein, such as blade blocks and ratcheting connectors, may be shown and described for use with a particular surgical retractor. However, blade blocks and ratcheting connectors may be used with other suitable surgical retractors including some that may be shaped differently or include a different number of frame segments than those described herein.

What is claimed is:

1. An adjustable surgical retractor frame comprising:
   a first frame segment including a middle section disposed between a first end and a second end;
   a second frame segment including an intermediate section and a pair of end sections projecting from the same side of the intermediate section, said pair of end sections maintaining a substantially parallel orientation with respect to each other, each of said pair of end sections including a top surface and a bottom surface;
   a pair of connectors, the pair of connectors being configured for coupling the first frame segment to the second frame segment so as to form said adjustable surgical retractor frame, each of the pair of connectors comprising:
     a ratchet housing configured for connecting to said first frame segment;
     a channel formed within the ratchet housing, the channel being configured to receive one of the pair of end sections of said second frame segment when the channel is aligned about parallel with said one of the pair of end sections but vertically offset therefrom and then the relative vertical position between the channel and said one of the pair of end sections is changed so that said one of the pair of end sections is received within the channel; and
     a ratchet fastener configured for releasably holding the one of the pair of end sections of said second frame segment within said channel.

2. The adjustable surgical retractor frame of claim 1, each of the pair of connectors further comprising a lock operable by a user to actuate the ratchet fastener so as to provide access to the channel and allow said one of the pair of end sections of said second frame segment to be received within the channel.

3. The adjustable surgical retractor frame of claim 1, wherein said ratchet housing includes one or more grooves or ridges formed therein, the one or more grooves or ridges being disposed within said channel, said one of the pair of end sections of said second frame segment including a complementary feature to said one or more grooves or ridges.

4. The adjustable surgical retractor frame of claim 3, wherein an interaction between the one or more grooves or ridges and the complementary feature enables a user to properly seat said one of the pair of end sections of said second frame segment within the channel when an intended one of either said top surface or said bottom surface is received within said channel, but prevents the user from seating said one of the pair of end sections of said second frame segment within the channel when an unintended one of either said top surface or said bottom surface is received within said channel.

5. The adjustable surgical retractor frame of claim 4, the channel of each of said pair of connectors being shaped to receive the top surface of the one of the pair of end sections of said second frame segment when forming said adjustable surgical retractor frame;
   wherein said first frame segment has a width that is no more than about 75% of a width of the second frame segment.

6. The adjustable surgical retractor frame of claim 1, the first end of said first frame segment being part of an extended substantially straight first end section and the second end of said first frame segment being part of an extended substantially straight second end section;
   the first end section and the second end section being outwardly canted away from each other at an angle suitable to reduce a risk of racking when expanding the adjustable surgical retractor frame formed upon coupling the first frame segment and the second frame segment together.

7. The adjustable surgical retractor frame of claim 6, wherein said angle is between about 0.01° to about 1.30°.

8. The adjustable surgical retractor frame of claim 1, wherein said ratchet housing is welded to one of the first end and the second end of said first frame segment.

9. The adjustable surgical retractor frame of claim 1, wherein said ratchet housing is configured to be manually attached to said first frame segment or manually detached from said first frame segment.

10. The adjustable surgical retractor frame of claim 1, further comprising:
    at least one blade assembly, the at least one blade assembly including a blade including a front blade face, the front blade face configured so as to be disposed adjacent a tissue wall of a wound or incision;
    at least one blade block configured for mounting the at least one blade assembly on said adjustable surgical retractor frame, the blade block configured for selectively orienting the front blade face in the direction of said tissue wall.

11. An adjustable surgical retractor frame comprising:
    a first frame segment including a middle section disposed between a first end and a second end;
    a second frame segment including an intermediate section and a pair of end sections projecting from the same side of the intermediate section, said pair of end sections maintaining a substantially parallel orientation with respect to each other, each of said pair of end sections including a top surface and a bottom surface;
    a pair of connectors, the pair of connectors configured for coupling the first frame segment to the second frame segment in order to form said adjustable surgical retractor frame, each of the pair of connectors comprising:

a ratchet housing configured for connecting to said first frame segment;

a channel formed within the ratchet housing, the channel being configured to receive one of the pair of end sections of said second frame segment when a ratchet fastener is actuated so as to expose the channel for receiving said one of the pair of end sections and the pair of connectors are vertically overlaid upon said pair of end sections; and said ratchet fastener being configured for releasably holding the one of the pair of end sections of said second frame segment within said channel.

12. The adjustable surgical retractor frame of claim 11, wherein said channel is disposed at an angle relative to said one of the end sections so as to reduce a risk of racking when expanding or contracting the retractor frame.

13. The adjustable surgical retractor frame of claim 12, said channel being angled within said ratchet housing.

14. The adjustable surgical retractor frame of claim 12, the first end of said first frame segment being part of an extended substantially straight first end section and the second end of said first frame segment being part of an extended substantially straight second end section;

the first end section of the first frame segment and second end section of the first frame segment extending from the same side of the middle section, the first end section and the second end section being outwardly canted away from each other so as to position said channel at said angle.

15. The adjustable surgical retractor frame of claim 12, said angle being between about 0.20° to about 0.76°.

* * * * *